United States Patent
Littwin et al.

(10) Patent No.: US 12,386,938 B2
(45) Date of Patent: Aug. 12, 2025

(54) AUTHENTICATION USING A BIOMETRIC TEMPLATE RELATED TO NEURAL ACTIVITY, AND APPLICATIONS THEREOF

(71) Applicant: COGNTIV Neurosystems Ltd., Tel-Aviv (IL)

(72) Inventors: Gideon Littwin, Tel-Aviv (IL); Hagai Lalazar, Tel-Aviv (IL); Nizan Klinghoffer, Giv'atayim (IL); Jonathan Berrebi, Tel-Aviv (IL); Ilay Gordon, Ramat Gan (IL)

(73) Assignee: COGNTIV Neurosystems Ltd., Tel-Aviv (IL)

( * ) Notice: Subject to any disclaimer, the term of this patent is extended or adjusted under 35 U.S.C. 154(b) by 0 days.

(21) Appl. No.: 19/003,945

(22) Filed: Dec. 27, 2024

(65) Prior Publication Data

US 2025/0217465 A1    Jul. 3, 2025

Related U.S. Application Data

(60) Provisional application No. 63/616,165, filed on Dec. 29, 2023.

(51) Int. Cl.
*G06F 21/32* (2013.01)
*G16H 40/63* (2018.01)

(52) U.S. Cl.
CPC ............. *G06F 21/32* (2013.01); *G16H 40/63* (2018.01)

(58) Field of Classification Search
None
See application file for complete search history.

(56) References Cited

U.S. PATENT DOCUMENTS

| | | | |
|---|---|---|---|
| 2012/0069247 A1 | 3/2012 | Morikawa et al. | |
| 2018/0125386 A1 | 5/2018 | Lim et al. | |
| 2020/0201974 A1* | 6/2020 | Xiong | G06F 21/31 |
| 2020/0349243 A1* | 11/2020 | Mullins | G06F 21/32 |
| 2022/0051039 A1* | 2/2022 | Chowdhury | A61B 5/38 |

(Continued)

OTHER PUBLICATIONS

Bidgoly AJ, Bidgoly HJ, Arezoumand Z. Towards a universal and privacy preserving EEG-based authentication system. Scientific Reports. Feb. 15, 2022;12(1):2531. (Year: 2022).*

(Continued)

*Primary Examiner* — James R Turchen
(74) *Attorney, Agent, or Firm* — Sterne, Kessler, Goldstein & Fox, P.L.L.C.

(57) ABSTRACT

In an embodiment, a computer-implemented method for decoding neural activity is provided. In the method, at least one machine learning model is trained using a training data set of EEG data and concurrently collected environmental data collected from data collection participants. Once the at least one machine learning model is trained, EEG data measured from sensors attached to or near a user's head is received. Environmental data describing stimulus the user is exposed to concurrently with the measurement of the EEG data is also received. The EEG data and the environmental data is input into the at least one machine learning model to determine an inference related to the neural activity. Based on the inference, an operation of a computer program is altered.

9 Claims, 22 Drawing Sheets

(56) References Cited

U.S. PATENT DOCUMENTS

| | | | |
|---|---|---|---|
| 2023/0099519 A1* | 3/2023 | Beltran | G16H 50/20 |
| | | | 600/300 |
| 2023/0191073 A1 | 6/2023 | Poltorak | |
| 2024/0372860 A1* | 11/2024 | Singh | H04L 63/10 |

OTHER PUBLICATIONS

Gopal SR, Shukla D. Concealable biometric-based continuous user authentication system an EEG induced deep learning model. In2021 IEEE International Joint Conference on Biometrics (IJCB) Aug. 4, 2021 (pp. 1-8). IEEE. (Year: 2021).*

Kamaraju SP, Das K, Pachori RB. EEG Based Biometric Authentication System Using Multivariate FBSE Entropy. Authorea Preprints. Oct. 31, 2023. (Year: 2023).*

Xu J, Zhou E, Qin Z, Bi T, Qin Z. Electroencephalogram-Based Subject Matching Learning (ESML): A Deep Learning Framework on Electroencephalogram-Based Biometrics and Task Identification. Behavioral Sciences. Sep. 14, 2023;13(9):765. (Year: 2023).*

Jayarathne I, Cohen M, Amarakeerthi S. BrainID: Development of an EEG-based biometric authentication system. In2016 IEEE 7th Annual Information Technology, Electronics and Mobile Communication Conference (IEMCON) Oct. 13, 2016 (pp. 1-6). IEEE. (Year: 2016).*

Mao Z, Yao WX, Huang Y. EEG-based biometric identification with deep learning. In2017 8th International IEEE/EMBS Conference on Neural Engineering (NER) May 25, 2017 (pp. 609-612). IEEE. (Year: 2017).*

International Search Report and Written Opinion for International Application No. PCT/IB2024/063235, mailed on May 13, 2025, 17 pages.

* cited by examiner

AUTHENTICATION USING A BIOMETRIC TEMPLATE RELATED TO NEURAL ACTIVITY, AND APPLICATIONS THEREOF

TECHNICAL FIELD

This disclosure generally relates to detecting and interpreting neural activity.

BACKGROUND

Electroencephalography (EEG) is a method to record an electrogram of electrical activity of a brain. EEG involves placing non-invasive electrodes on or near the head, such as on the head, on the forehead, inside or around the ears. Neurons in the underlying brain tissue generate electrical activity in the form of ionic currents that can be measured as voltage differences in the electrodes. These voltage changes are recorded and can vary in accordance with the orientation and distance to the source of the activity. The value recorded is distorted by intermediary tissues and bone that can act as resistors and capacitors in an electrical circuit. EEG is used to diagnose sleep disorders, epilepsy, brain tumors, brain damage from head injury, inflammation of the brain (encephalitis), and stroke.

EEG data can, for example, be collected using a specially designed head strap. EEG head straps are devices that attach electrodes to the scalp to measure the electrical activity of the brain. They can be used for various purposes, such as enhancing productivity, monitoring digital health at home, or facilitating drug discovery. For example, EEG head straps can help users to optimize their cognitive performance, mood, and focus by providing neurofeedback. They can also enable users to track their brain health, stress levels, and sleep quality by sending data to their smartphones or computers. Moreover, EEG head straps can assist researchers and clinicians to test the effects of new drugs or treatments on the brain by recording the changes in digital biomarkers.

A wearable computer, also known as a body-borne computer, is a computing device worn on the body. Some wearable computers are worn on the head, such as smart headphones, or as part of a helmet.

Among head mounted computers, there has been growing interest and development in headsets or glasses, at least in part to support interface with immersive 3D content. The immersive 3D content can include augmented and virtual reality.

A virtual reality headset (or VR headset) is a head mounted device that provides virtual reality for the wearer. VR headsets are used, for example, with video games, simulators, and trainers. VR headsets typically include a stereoscopic display (providing separate images for each eye), stereo sound, and sensors like accelerometers and gyroscopes for tracking the pose of the user's head to match the orientation of the virtual camera with the user's eye positions in the real world. Some VR headsets also have eye-tracking sensors, face-tracking sensors, hand-tracking sensors, and gaming controllers.

Augmented reality (AR) is an interactive experience that combines real world and computer-generated content. Some VR headsets can also provide an AR experience by incorporating video captured from a front-facing camera. An AR experience can also be provided by some smart glasses. Smart glasses are eye or head worn wearable computers that offer useful capabilities to the user and often include displays that add information overlaying what the wearer sees.

These VR/AR devices often lack a keyboard or touchscreen display that most general-purpose desktop computers and mobile devices have. Other techniques are used to provide input into these devices. Some devices have controllers that users can move in space similar to a computer mouse. The movement is tracked to, for example, control a pointer on the device. The controllers can have other buttons to, for example, select items. Similarly, some devices have controllers with joysticks.

These VR/AR devices can use other techniques to input data as well. These techniques can include speech recognition, eye tracking, and gesture recognition. Speech recognition is a capability which enables a program to process human speech into a written format. Eye tracking is a sensor technology that can detect a person's gaze and therefore follow what they are looking at in real-time. The technology converts eye movements into a data stream that contains information such as pupil diameter, the gaze vector for each eye, and gaze point. Gesture recognition uses computer vision to recognize a bodily motion or state, such as from a user's face or hand. To use gesture recognition, the devices can overlay a display with virtual buttons and content, and a user can use gestures to select or manipulate items.

Each of these different input techniques have their own limitations. For example, the amount of information that a user can input in a given time may be limited, and the effort on the part of the user to input the information may be great. In other examples, the accuracy of detection may be limited and the interaction required may be non-intuitive for a user. The actions required of the user may be awkward or cumbersome. The actions may be very tiring on the muscles and may not be private.

To authenticate a user, some head mounted devices may have hardware components that illuminate and measure the user's eye to use iris or retinal scanning as an authentication method. That may not work for smart glasses where the hardware needs to be placed into a restricted form factor. Another example is to type a pin code using the interfaces described above.

For these various input techniques, additional hardware or devices may be needed, and that additional hardware may be expensive. For example, to conduct eye tracking or hand tracking, sensors are needed that are difficult to miniaturize to the size of glasses. An additional challenge is that the computation to process the information from these sensors is difficult achieve in a small form factor.

Improved methods are needed to input information into a computer, particularly a head mounted computer, and to detect and analyze EEG data.

SUMMARY

In an embodiment, a computer-implemented method for authenticating a user is provided. During enrollment, a first electroencephalogram (EEG) data collected from sensors attached to or near the user's head is received. The first EEG data is input into at least one machine learning model to determine a first biometric template related to neural activity. The at least one machine learning model was previously trained using a training data set of additional EEG data from data collection participants to maximize distinctiveness. During authentication, a second EEG data measured from the sensors attached to or near the user's head is received. The second EEG data is input into the at least one machine learning model to determine a second biometric template related to the neural activity. The first and second biometric templates are compared to determine the user's identity.

Systems and computer program product embodiments are also disclosed.

Certain embodiments of the invention have other steps or elements in addition to or in place of those mentioned above. The steps or elements will become apparent to those skilled in the art from a reading of the following detailed description when taken with reference to the accompanying drawings.

BRIEF DESCRIPTION OF THE DRAWINGS

The accompanying drawings, which are incorporated herein and form a part of the specification, illustrate embodiments of the present disclosure and, together with the description, further serve to explain the principles of the disclosure and to enable a person skilled in the arts to make and use the embodiments.

In the drawings, like reference numbers generally indicate identical or similar elements. Additionally, generally, the left-most digit(s) of a reference number identifies the drawing in which the reference number first appears.

DETAILED DESCRIPTION

Figure 1:
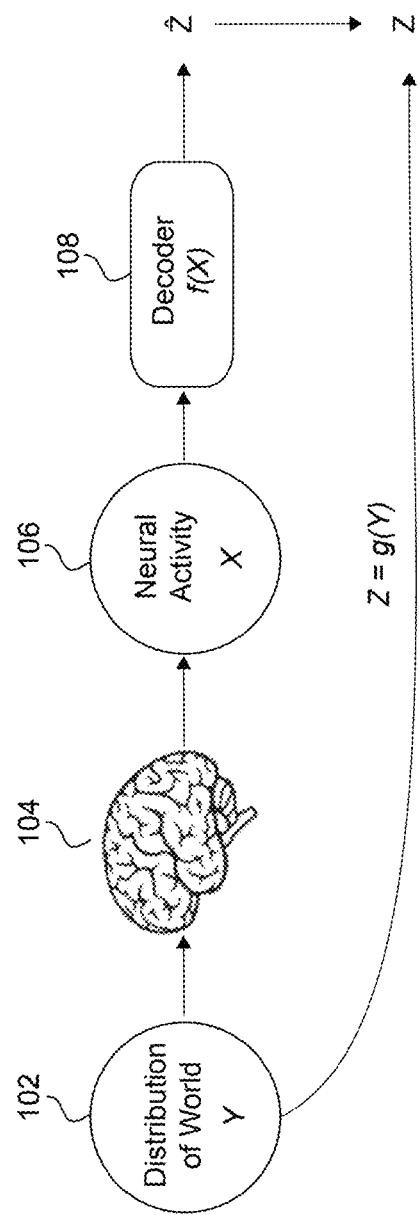
FIG. 1 is a diagram illustrating a neural decoding procedure.

FIG. 1 is a system 100 illustrating a known, simple method to attempt to decode neural activity. Diagram 100 illustrates a distribution of a world 102, a brain 104, neural activity 106, and a decoder 108.

Distribution of world 102 represents stimuli presented to a subject. The stimuli is what the subject is exposed to and is able to sense, and may include visual auditory, tactile, proprioceptive, olfactory and gustatory inputs. For example, if the subject is viewing an image, the distribution of the world includes the set of all images that can be view. Distribution of world 102 may also include other nonvisual sensations that the user is exposed to, such as what the subject is hearing, touching, smelling and tasting.

A subject perceives world 102 through their senses, and the subject's nervous system communicates this information to the subject's cerebral cortex in brain 104. In particular, the subject's sensory organs (e.g., eyes, ears, skin, joints, muscles, nose, and mouth) transduce sensory information from the respective organs through the nervous system, finally arriving at the sensory cortices in the subject's brain 104, where sensory signals are processed and eventually interpreted (perceived).

Brain 104 includes billions of neurons. Each neuron is connected by synapses to several thousand other neurons. These neurons typically communicate with one another by means of fibers called axons, which carry trains of signal pulses called action potentials to other parts of the brain or body targeting specific recipient cells. Processing sensory signals involves sending and manipulating electrical signals between and within neurons in brain 104.

The electrical signals generated by brain 104 are generally very weak. To be detected on a subject's skin, the signals must also travel through the subject's soft tissue and skull. A human skull is only partially conducting, which further attenuates any electrical signals that may be collected.

As mentioned above, electroencephalography (EEG) attempts to capture these small electrical signals originating from the brain using a plurality of electrodes touching or around the skin on a subject's head. Each electrode captures a time series of voltage data illustrating changes in electrical potential at the point of contact with the skin. This time series data is collected as neural activity 106. This voltage data is generated as a result of an aggregate of neural activity during the relevant time period. Additionally or alternatively, neural activity 106 may be collected in other ways outside of EEG.

Decoder 108 attempts to interpret neural activity 106. For example, decoder 108 may attempt to determine what exists in world 102 and what from world 102 the subject would like to interact with. Making such a determination accurately and consistently is a very difficult problem, and in practice, decoder 108 in the configuration of FIG. 1 does not always resolve to the correct solution.

One reason why decoder 108 has such difficulty in interpreting what the subject would like to interact with is that the interaction possibilities of world 102 are so great. A virtually infinite amount of content and stimuli is available to brain 104. Also, our brains are very different from one another. Thus, creating decoder 108, which can be used for more than one individual, is very difficult.

Embodiments disclosed herein can dramatically increase accuracy of the determination. Some embodiments increase accuracy by recognizing that, in the context of head mounted computers, the distribution of world 102 is constrained and, similarly, can be used to constrain the evaluation needed from decoder 108. This is illustrated, for example, in FIG. 2.

Figure 2:
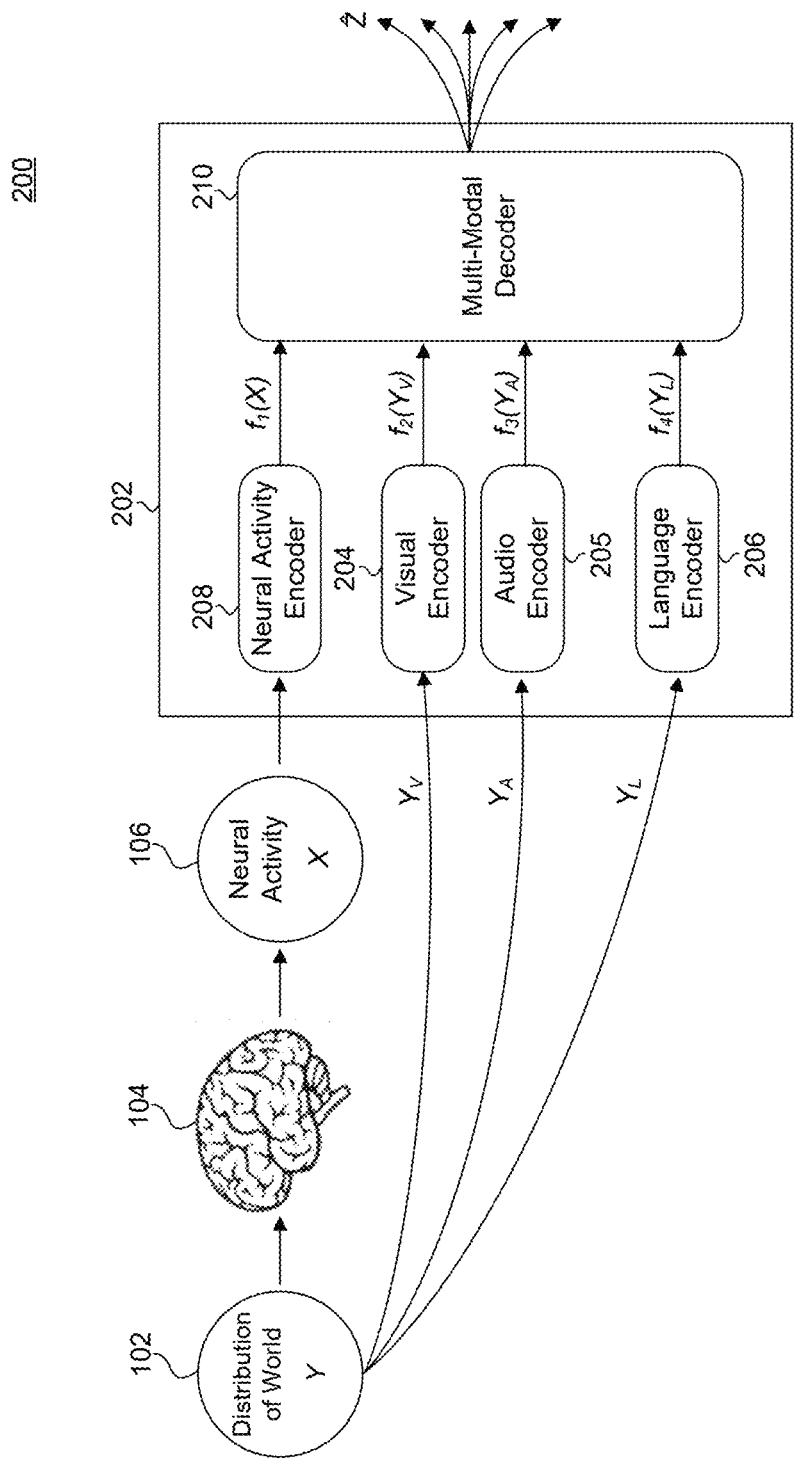
FIG. 2 is a diagram illustrating an example of a multi-modal neural decoding procedure including visual and audio decoders.

FIG. 2 is a diagram 200 illustrating an example of a multi-modal neural decoding procedure. Diagram 200 includes a neural activity decoder 202. Neural activity decoder 202 includes a neural activity encoder 208, visual encoder 204, audio encoder 205, language encoder 206, and a multi-model decoder 210.

Like diagram 100 in FIG. 1, brain 104 perceives world 102 and EEG information is captured as neural activity 106. Neural activity 106 is input into neural activity encoder 208. Neural activity encoder 208 accepts time series of EEG data captured. Neural activity encoder 208 encodes the EEG data X into $f_1(X)$. This is similar to visual encoder 204 and audio encoder 205. Neural activity encoder 208 is at least a portion of the machine learning algorithm. In an embodiment, neural activity encoder 208 may be at least a portion of a deep learning neural network, such as a convolutional neural networks (CNN) or recurrent neural networks (RNNs), such as long short-term memory (LSTM) and gated recurrent units (GRUs).

In contrast to system 100 in FIG. 1, in diagram 200, the stimuli the subject is exposed to—a sample taken from world 102—is also input into a machine learning model used to determine what the user's perceptions or intentions are from neural activity 106. The stimuli may be the collected from the same time period as neural activity 106. Using the stimuli in this manner constrains the evaluation needed by the machine learning algorithm.

For example, suppose a user is wearing augmented reality glasses, and the glasses display to the user a menu with three options. The three options may, for example, be three applications, such as a music, mail, and weather application. In that situation, the decoder does not need to determine what the user is looking at. The visual stimuli of the options the user is viewing are input directly into the machine learning model as $Y_V$. Thus, the machine learning algorithm only needs to decipher the user's intent. In this example, the machine learning algorithm only needs to determine from neural activity whether a user wants to select one of those three options and which option the user would like to select.

To input visual stimuli into the machine learning model, the system may include a visual encoder 204. In one embodiment, the visual stimulus input into visual encoder 204 may include still images or a video stream captured from a camera fixed to the head mounted computer. The camera may be positioned to capture what the user is viewing. This may be particularly useful in embodiments involving augmented reality.

Additionally or alternatively, the visual stimuli input into visual encoder 204 may include a stream from the device's operating system illustrating what is currently displayed to the user. The stream may include a mask indicating where on the screen relevant options are located. The mask may for example have data indicating which options are located at each pixel presented to the user. In this way, the mask can provide information about layout of the visual stimuli to visual encoder 204. In addition to the layout, additional information may be inputted to visual encoder 204 related to the options. Additional information can include, for example, the color of the options presented. In one embodiment, the camera and operating system display information can be input into visual encoder 204 using two separate streams. In another embodiment, the camera and operating system display information may be input into visual encoder 204 using a single stream.

Visual encoder 204 is at least a portion of the machine learning algorithm. In an embodiment, visual encoder 204 may be at least a portion of a deep learning neural network. In one example, visual encoder 204 may be a transformer neural network. A transformer is a deep learning model that adopts the mechanism of self-attention, differentially weighting the significance of each part of the input data. In other examples, visual encoder 204 may a transformer, CNN, or RNN.

In addition to visual stimuli, other stimuli may be input into the machine learning algorithm illustrated in FIG. 2. In particular, audio stimuli is input as illustrated by $Y_A$. Similar to visual encoder 204, audio encoder 205 is at least a portion of the machine learning algorithm. In an embodiment, audio encoder 205 may be at least a portion of a deep learning neural network, such as a transformer, CNN, or RNN.

Inputting audio stimulus $Y_A$ into the machine learning algorithm used to decode neural signals may be useful because it may further normalize and constrain the neural data. For example, when a subject hears their name, it may strongly capture the subject's attention, resulting in corresponding neural EEG signals. Without the audio data, the machine learning model may have incorrectly inferred the subject's perception or intention from the neural activity. However, with the audio data, the machine learning model may instead infer that this neural activity is merely the brain's response to the person's name being called.

In addition to audio and visual stimuli, natural language that the user is exposed to (whether it be audibly or visually) may also be input into the machine learning algorithm. The natural language stimuli is illustrated as $Y_L$ and is input into language encoder 206. Language encoder 206 may be is at least a portion of the machine learning algorithm. It make be at least a portion of a deep learning neural network, such as a transformer, CNN, or RNN. In one embodiment, language encoder 206 may be a large language model. A large language model (LLM) is an advanced type of artificial intelligence (AI) designed to understand, generate, and interact with human language. These models are trained on massive datasets, often including text from books, websites, and other written sources. The goal is for the model to learn patterns, structures, grammar, and meaning in language.

Language encoder 206 may tokenize natural language stimuli $Y_L$ and feed into the trained model to generate $f_4(Y_L)$.

As illustrated in diagram 200, visual encoder 204 generates $f_2(Y_V)$, audio encoder 205 generates $f_3(Y_A)$, and language encoder 206 generates $f_4(Y_L)$. All three may be input into a multi-modal decoder 210.

As mentioned above, the neural activity 106 may be collected simultaneous to when the user is exposed to stimulus $Y_V$ and $Y_A$. For example, every frame of visual and or audio stimuli input through the visual encoder 204 and 205 may correspond with a time series of EEG data. EEG typically has a sampling rate between 300-1,000 samples per second. Video is typically less, often between 24-120 frames per second. The EEG data can be aligned with the video input stream by associating the closest EEG sample with the concurrent video frame. Or, at least one of the streams can be resampled to account for another stream with a higher sampling rate.

Every time the decoding operation is conducted, a moving window of stimuli and EEG data may be input to the model. The moving window may be all the stimuli and EEG data measured from a set time period (may be from the previous 1, 2, 3, 10, or 30 seconds). If the stimuli has not changed since the last decoding step, there may be no need to re-execute the visual encoder 204. Instead, it may be possible to merely reuse visual encoder 204's output from the previous decoding operation.

Multi-modal decoder 210 accepts as input data from the four encoders—neural activity encoder 208 ($f_1(X)$), visual encoder 204 ($f_2(Y_V)$), audio encoder 205 ($f_3(Y_A)$) and language encoder 206 ($f_4(Y_L)$)—and generates, based on the input data, a determination as to neural activity. Multi-modal decoder 210 makes the neural activity determination using a combination of different modalities of data, where each modality is the representation of a single independent channel of sensory input between a device and a human.

Multi-modal decoder 210 is at least a portion of the machine learning algorithm. In an embodiment, neural activity encoder 204 may be at least a portion of a deep learning neural network configured to conduct a multimodal determination. One example algorithm is a multi-input transformer, CNN, or RNN.

As mentioned above, multi-modal decoder 210 uses available EEG data from the subject and data describing stimuli to which the subject is simultaneously exposed to make an inference as to neural activity. One possible type of inference from the neural activity is menu control. In that embodiment, the visual stimulus presented to the user may be a menu, and the neural activity detected may be whether a subject desires to select a menu option and, if a menu option is selected, which one the subject intends to select. In this way, embodiments allow a subject to make menu selections using their thoughts. In an example, the menu may be a keyboard, and using the same technique, a subject can make menu selections from the keyboard to spell out text.

In an embodiment, a movement of the subject may be inferred from the neural activity. In different examples, the movement may be hand gestures, eye movements, or facial expressions. For example, the gestures may detect the user handwriting text. In other examples, the movement may be saccadic eye movement.

In another embodiment, the neural activity detected may be imagined speech. The neural activity detected may be at least a portion of the subject's intended, yet unspoken, speech. For example, if the neural activity detected may be the user imagining a particular word or phrase.

In yet another embodiment, a user's identity may be inferred from the neural activity. In particular, a brain biometric template may be generated using the neural activity decoder. The brain biometric template may be used in a number of different ways including to verify the user's identity. This is described in greater detail below with respect to FIGS. 17 and 19.

Figure 3:
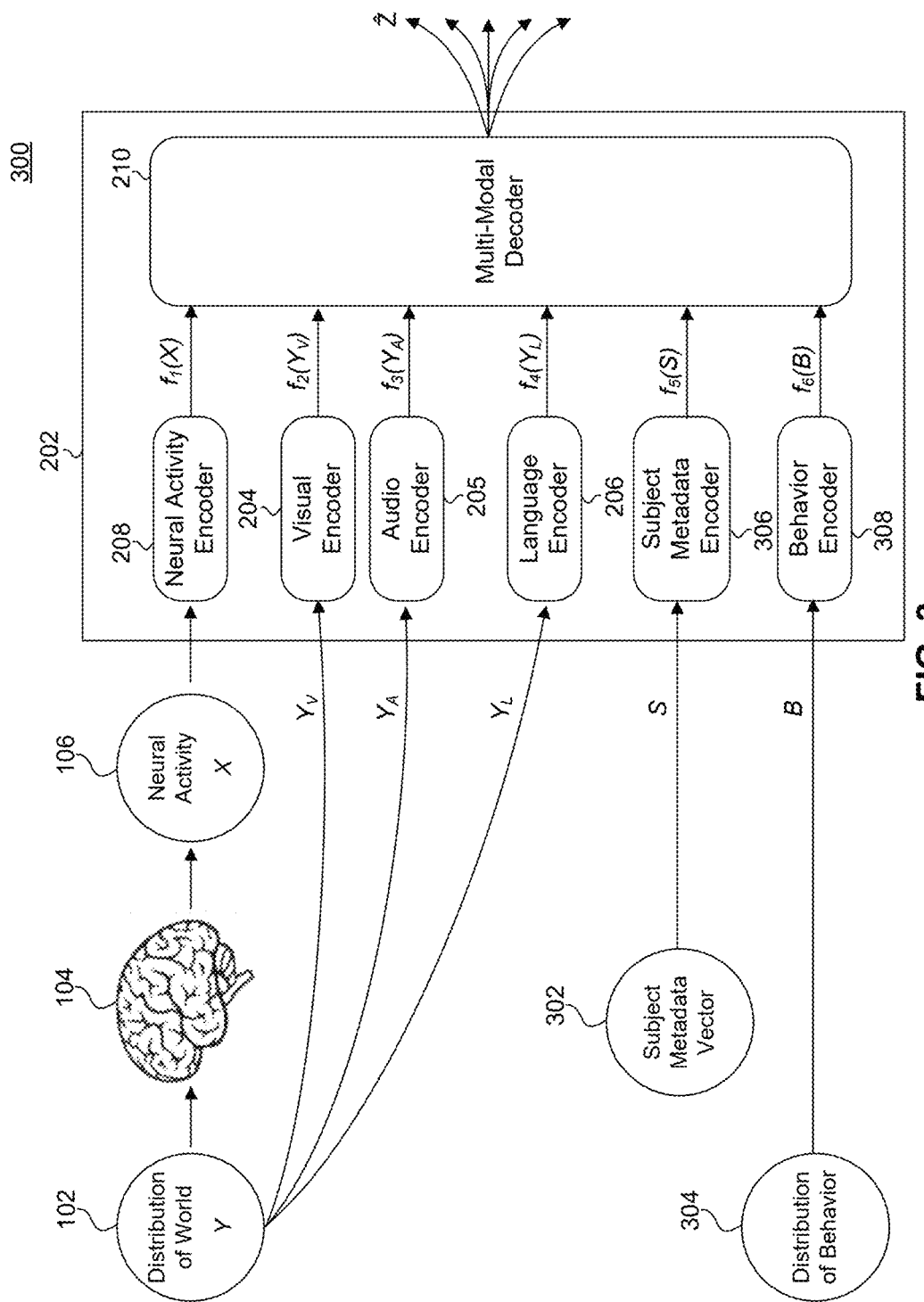
FIG. 3 is a diagram illustrating an example of a neural decoding procedure enhanced by a distribution of behavior and subject embedding.

FIG. 3 is a diagram 300 illustrating an example of a neural decoding procedure enhanced by auxiliary information. Like in diagram 200, diagram 300 includes visual encoder 204, audio encoder 205, and language encoder 206. Diagram 300 further includes auxiliary information, such as subject metadata vector 302 and distribution of behavior 304.

Subject metadata vector 302 represents information available about the subject user. Subject metadata vector 302 may include metadata such as the subject's gender (e.g., male or female), the subject's birthdate (and hence age), the subject's handedness (right-handed or left-handed), the subject's genetic sequencing, and subject's multiomics data. Subject metadata vector 302 may represent data that does not change over time. The subject may provide the information on registration, and every time the subject uses the system, after the subject is identified (perhaps using the authentication method described below with respect to FIGS. 17 and 19), subject metadata vector 302, which describes the information provided, is loaded.

In addition to the neural activity information and the visual and audio encoder information, subject metadata vector, S, 302 is provided. The subject metadata vector 302 is input to the subject metadata encoder 306, which generates the representation $f_5(S)$. This representation is input to neural activity decoder 202 to be used for inference on neural activity.

System 300 also includes distribution of behavior, B, 304. While the distribution of world 102 represents what the user is stimulated with and subject metadata vector 302 represents aspects of who the user is, distribution of behavior 304 describes the set of actions the user may be doing. In an embodiment, distribution of behavior 304 may include information from a headset's eye tracker. Additionally or alternatively, distribution of behavior 304 may include hand tracking if the device has that capability. Distribution of behavior 304 can include data from other biosensors on the subject, such as the subject's heart rate.

The distribution of behavior 304 is input to the behavior encoder 308, which generates the representation $f_6(B)$. This representation is used by the neural activity decoder 202 for inference on a user's neural activity.

Similar to the stimulus data $Y_V$ and $Y_A$, a moving window of behavior data B may be used. The moving window may be all the behavior data collected from a set time period (may be from the previous 1, 2, 3, 10, or 30 seconds). This moving window is input into behavior encoder 308, which generates $f_6(B)$. Every time the decoding operation is conducted, the moving window of stimulus, behavior, and EEG data, along with subject metadata vector 302 may be input to neural activity decoder 202.

As with visual encoder 204 and audio encoder 205, subject metadata encoder 306 and behavior encoder 308 may be at least a portion of a machine learning model.

Figure 4:
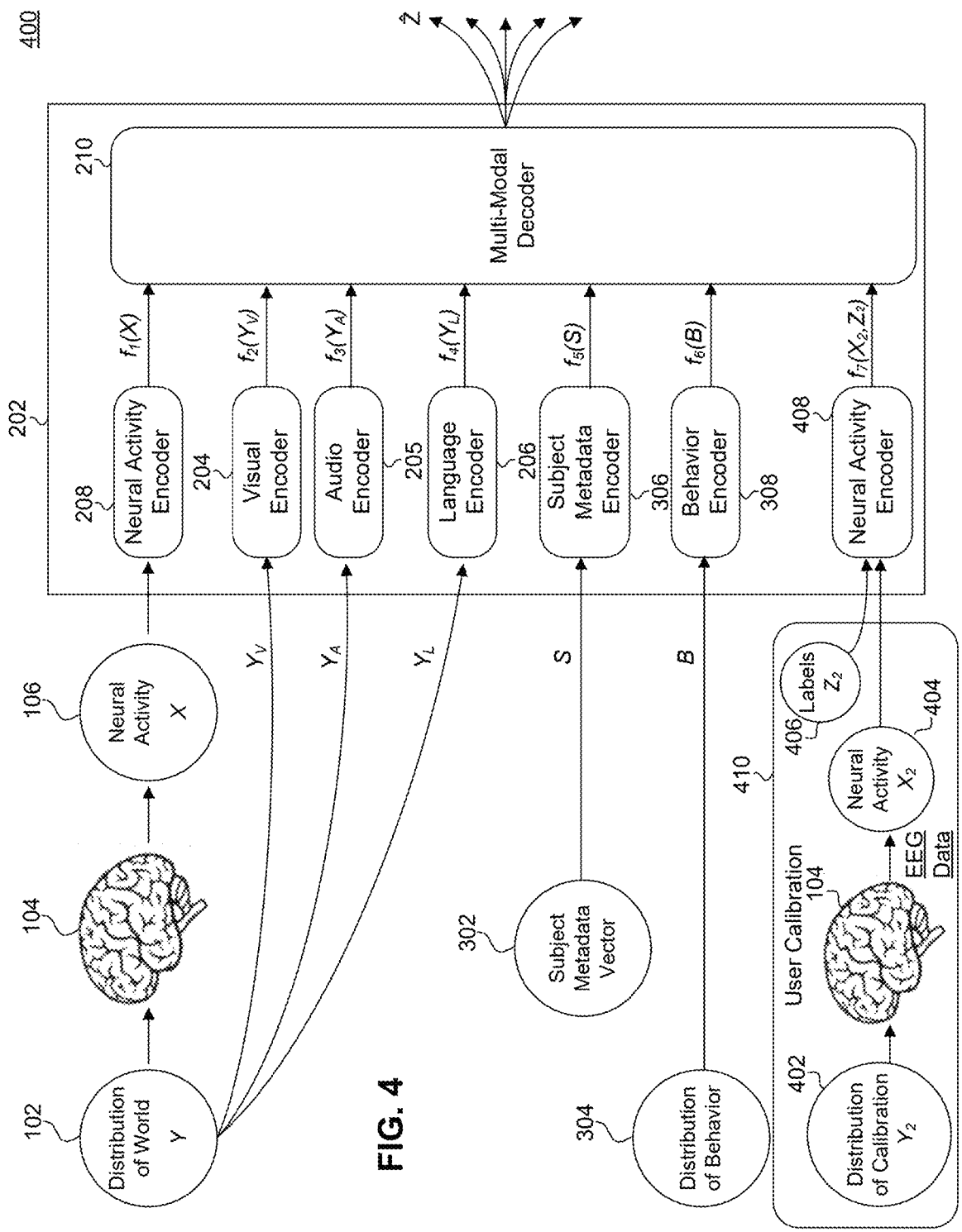
FIG. 4 is a diagram illustrating an example of a neural decoding procedure with a user calibration.

FIG. 4 is a system 400 illustrating an example of a neural decoding procedure with a user calibration. People's brains vary greatly. The calibration process illustrated in system 400 helps neural decoder 202 adapt to the unique neural activity patterns of individual subjects' respective brains. Calibration may occur once when the user is first registering in the system, and may be infrequently updated as the subject's brain ages or changes over time.

User calibration module 410 includes a distribution of calibration 402 ($Y_2$). Distribution of calibration 402 represents stimuli presented to the user during the calibration process. In an embodiment, the stimuli may resemble the stimuli presented during distribution of world 102, and the calibration may mimic the task ultimately decoded by neural activity decoder 202.

For example, during calibration, system 400 may display a plurality of different applications in a menu format on a screen. During calibration, one application may pop up at a time. Suppose there are three different applications, a messaging application, email application, and search application. The option for the messaging application is displayed and then disappears (e.g., fades in and out). Then, the option for the mail application is displayed and then disappears (e.g., fades in and out). Then, the option for the search application is displayed and then disappears (e.g., fades in and out).

The display of the calibration stimulus is observed by the subject and stimulates the subject's brain 104. EEG (neural data 404 is collected from the user while the stimulus is being applied. As described above, EEG data 404 is time series data of voltage information collected from EEG sensors on the subject's head.

EEG data 404 ($X_2$) has corresponding labels 406 ($Z_2$) that indicate what distribution of calibration stimulus 402 is being supplied at the time the respective EEG data 404 is collected. In this way, in the example above, EEG data 404 is labeled according to what is happening on the screen at the time the EEG data 404 is recorded. In the example above, a time series of EEG data 404 may be labeled indicating that the messaging application is displayed when that time series is collected; a time series of EEG data 404 may be labeled indicating the mail application is displayed when that time series is collected; and a time series of EEG data 404 may be labeled indicating the search application is displayed when that time series is collected.

EEG data 404 and corresponding labels 406 are input into another neural activity encoder 408. Neural activity encoder 408 is at least a portion of the machine learning algorithm. In an embodiment, neural activity encoder 408 may be at least a portion of a deep learning neural network, such as a transformer neural networks, convolutional neural networks (CNN), or recurrent neural networks (RNNs), such as long short-term memory (LSTM) and gated recurrent units (GRUs). Neural activity encoder 408 generates a value $f_7(X_2, Z_2)$ that is used by multi-modal decoder 210.

Figure 5:
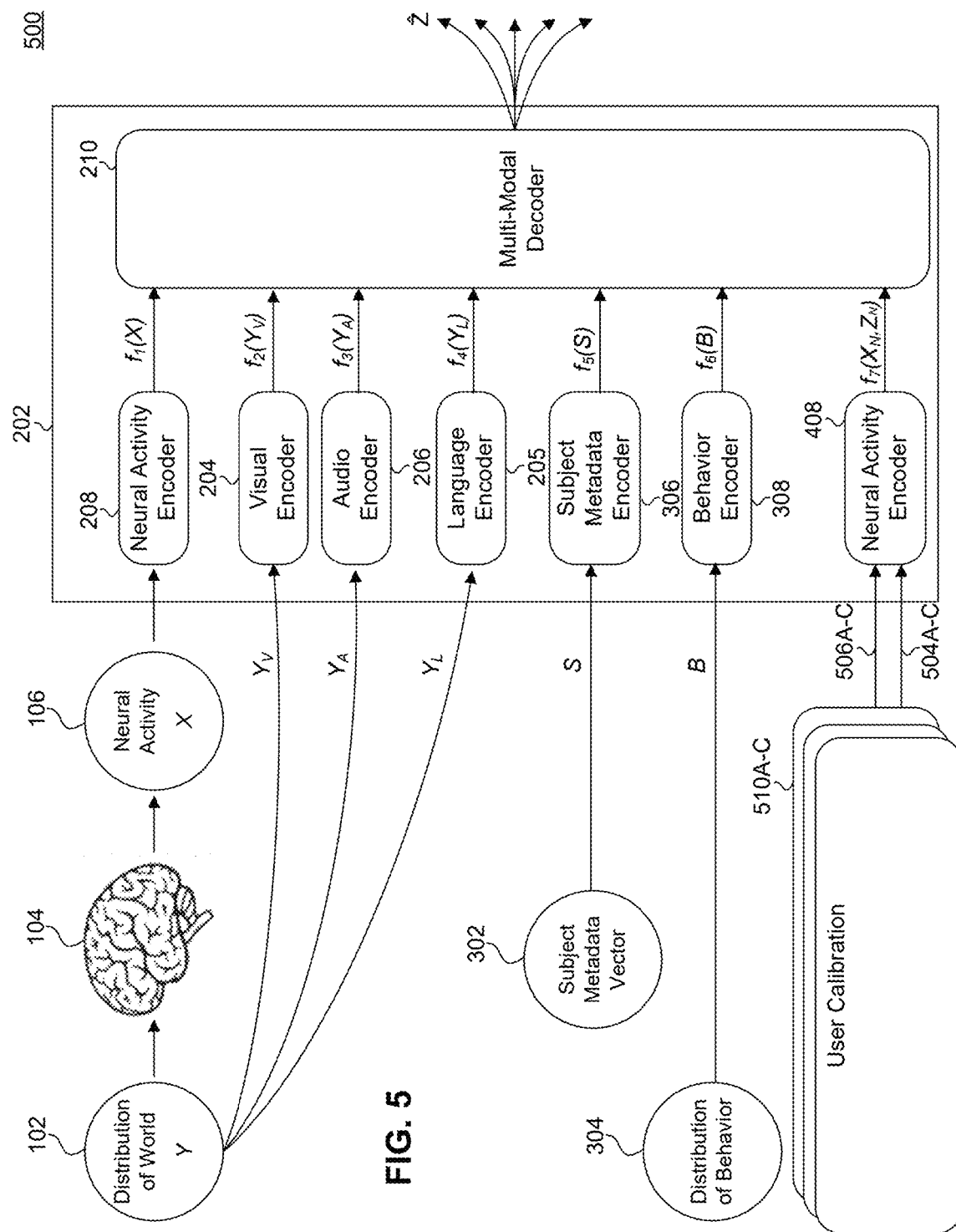
FIG. 5 is a diagram illustrating an example of a neural decoding procedure including multi-task user calibrations.

FIG. 5 is a system 500 illustrating an example of neural decoding procedure including multiple user calibrations. According to an embodiment, providing calibration with the user performing one type of task (e.g., menu selection) may increase accuracy to detect another different type of task (e.g., hand gestures).

In an embodiment, user calibration modules 510A-C each provide a different type of calibration task, resulting in more varied neural patterns from the subject's brain 104. For example, user calibration module 510A may ask the user to remain idle, user calibration module 510B may present various menu options as described above, and user calibration module 510C may ask the user to complete a movement, such as a facial or hand gesture.

As described above for system 400, each of user calibration modules 510A-C collects corresponding EEG data 504A-C and assigns corresponding labels 506A-C that indicate what calibration stimulus is being supplied, or behavior was executed, at the time the respective EEG data is collected. Additionally or alternatively, user calibration module 510A-C may ask a subject to conduct multiple tasks simultaneously (e.g., select menu options while conducting gestures). In this way, a single composite calibration task can achieve multiple EEG-label pairings within the same task.

EEG data 504A-C and corresponding labels 506A-C are input into a neural activity encoder 408. The neural activity encoder 408 is at least a portion of the machine learning algorithm, and may be at least a portion of a deep learning neural network, such as a transformer neural networks, convolutional neural networks (CNN), or recurrent neural networks (RNNs), such as long short-term memory (LSTM) and gated recurrent units (GRUs). Neural activity encoder 508 generates a value $f_7(X_N, Z_N)$ that is used as an input to multi-modal decoder 210.

The following description is divided into four sections. First, how the model is trained as described with respect to FIGS. 6, 7A-B, and 8A-C. Second, calibration is described with respect to FIGS. 9-12. Third, authentication using a brain biometric template. Fourth, determining a condition using the brain general representation as described with respect to FIGS. 17-20. Fifth and finally, different system components are described in greater detail with respect to FIGS. 21 and 22.

Training a Neural Decoder

Figure 6:
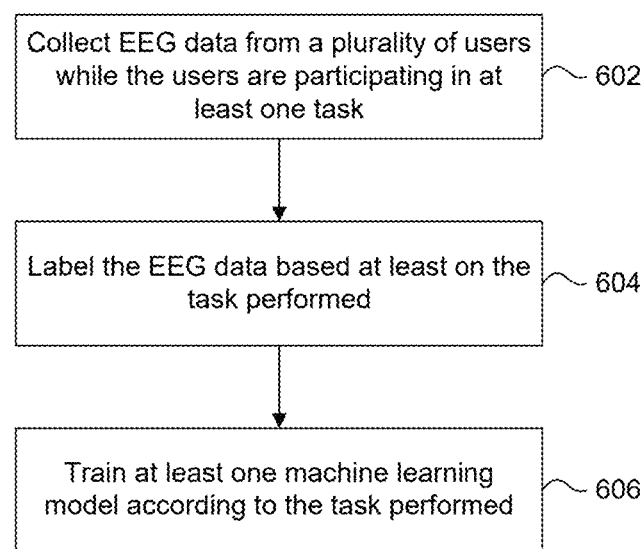
FIG. 6 is a flowchart illustrating a method of training a machine learning model using EEG data.

FIG. 6 is a flowchart illustrating a method 600 of training a machine learning model using EEG data.

Method 600 begins at 602 by collecting EEG data from a plurality of subjects while the respective subjects are participating in at least one task. The EEG data may be collected from any EEG device, including a head mounted device, as illustrated with respect to FIGS. 7A-D. In an embodiment, the data collection at step 602 for training may involve higher density of sensors on the head than may be used after training for inference. For example, the data collection may include 512 sensors. In addition, additional display devices and speakers pay be provide additional stimuli.

Figure 7A:
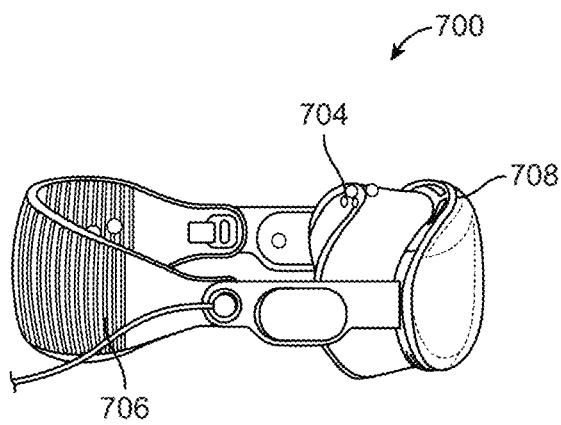
FIGS. 7A-D each illustrate a head mounted device that is configured to measure EEG data that can be used to perform a neural decoding procedure.

FIGS. 7A-D each illustrate a head mounted device with EEG sensors which allows performance of a neural decoding procedure. FIG. 7A illustrates a mixed reality device 700 including a front display portion 708 and a strap 706. Front display portion 708 and strap 706 can include EEG sensors 702 and 704.

Figure 21:
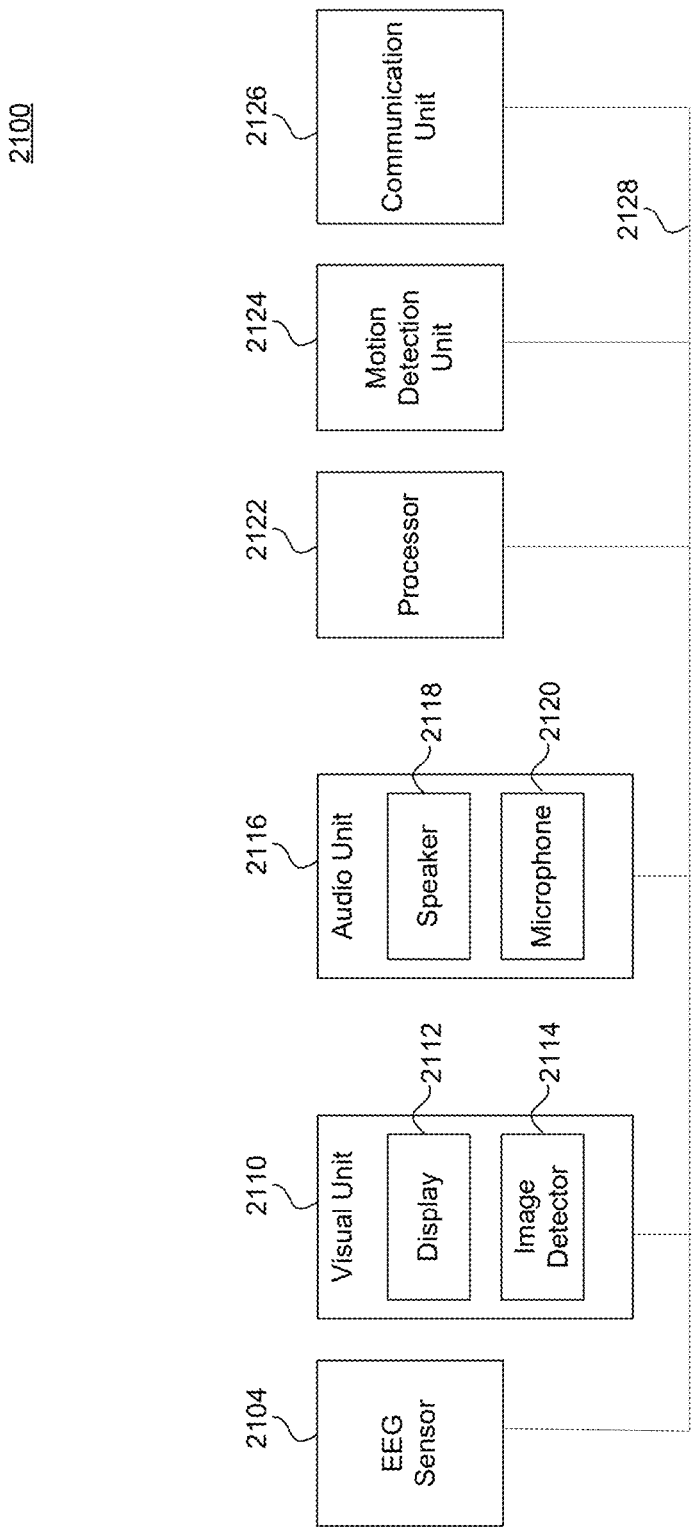
FIG. 21 is a diagram illustrating a computing device used on the head mounted device.

Front display portion 708 may encase any or all of the electronic components illustrated in FIG. 21. Front display portion 708 may include for example a stereoscopic display, stereo sound, and head-motion-tracking sensors, which may include devices such as gyroscopes or accelerometers.

Strap 706 is configured to hold front display portion 708 on a user's head. Strap 706 may be flexible and adjustable to adapt to different size heads. Strap 706 may also include electronic components (such as a single wire or communication bus) to transport electronic information collected from the EEG sensors 704 to a processor (not shown) within front display portion 708.

EEG sensors 704 include electrodes sitting on the user's head, in particular the user's forehead, side, and back of the head. The electrodes can be configured to extend through the hair. For example, EEG sensors 704 may be comb electrodes. They may have depth sufficient to go through hair like a comb and touch the scalp. EEG sensors 704 sit on the forehead or the temples where the user typically lacks much hair. The electrodes measure voltage changes on the skin. EEG sensors 704 each may include a small chip that has some electronics, such as an analog-to-digital converter, that connects to the bus of the system.

The voltage measured on the head by EEG sensors 704 emanate from electrical dipoles resulting from the brain's electrical activity. EEG sensors 704 are configured to detect signals from the brain of the user. They may also detect other signals from other biosignal sources like the muscles in in the user's face. For example, users have large jaw muscles, which are activated when a subject makes facial gestures, speaks, or chews. The activation of these muscles changes the electrical field which can be measured by the electrodes on the subject's head. In another example, the user has eye muscles, and the eye itself can be modeled as an electrical dipole. As the eye rotates, this electrical dipole changes the electrical field measured by the EEG sensors 704.

Figure 7B:
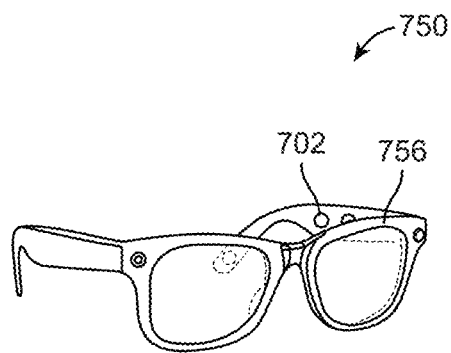

In addition to mixed reality device 700 in FIG. 7A, EEG sensors may be integrated into the arms of smart or augmented reality glasses 750 in FIG. 7B. In contrast to mixed reality device 700, augmented reality glasses 750 are designed to fit as much capability into a form factor and weight that is typical of conventional glasses and sunglasses. A computer with components described below with respect to FIG. 21 may be located inside the arms of these glasses.

EEG sensors may be located within an arm 756 on each side of augmented reality glasses 750, or may be located with a strap that runs behind or around user's head and attaches to the respective arms of augmented reality device 750.

Figure 7C:
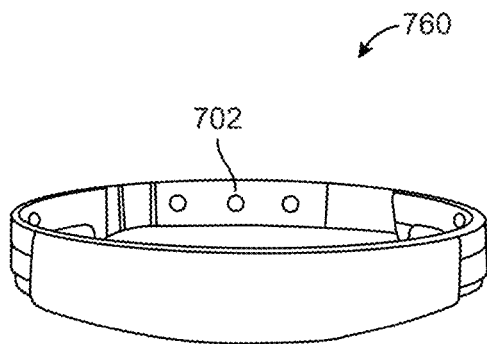
Figure 7D:
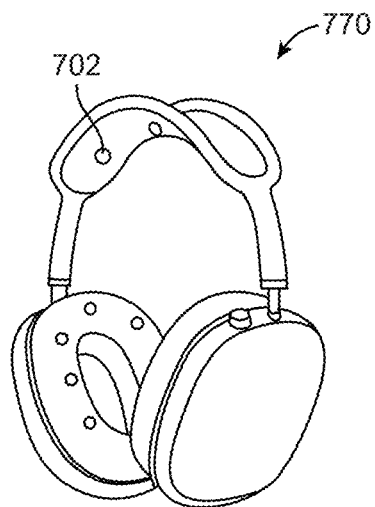

In addition to head mounted devices, EEG sensors may be integrated into a band or strap that goes on the forehead, back of the head, crown of the head, or completely surrounding the head as illustrated by head strap 760 in FIG. 7C.

In addition to the above, EEG sensors may be integrated into headphones. EEG sensors may be integrated into the soft cup and upper band of over-the-ear headphones 770 in FIG. 7D, or located within or around the ear by integration with earbud headphones.

Turning to FIG. 6, EEG data is collected and recorded from a subject at step 602 while the subject performs a task. At 604, the EEG data is labeled based on the task performed. Examples of tasks are illustrated in FIGS. 8A-D.

Figure 8A:
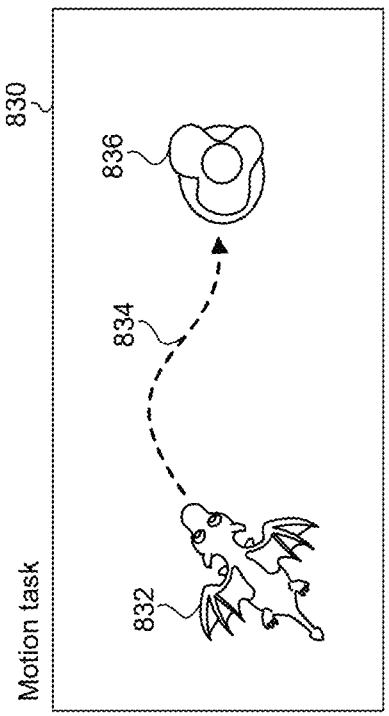
FIGS. 8A-D are examples of tasks that are used to collect EEG data and train a machine learning model.

FIG. 8A illustrates a screen presented to a user while performing an idle task 800. During this time, the subject is just sitting idly, resting, and not doing anything active. In some idle tasks the subject has their eyes open, and in others the subject is instructed to close their eyes. This data may be particularly useful in training a model for an identification task, as described below with respect to FIG. 17.

Figure 8B:
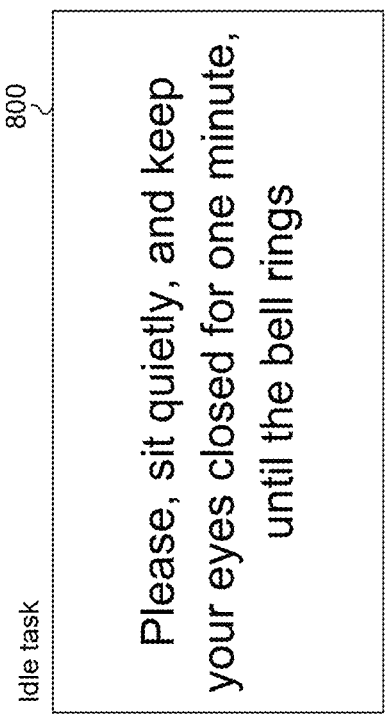

FIG. 8B illustrates a motion task 830. While performing motion task 830, the subject controls an avatar 832 and navigates avatar 832 along a path 834 to a target 836. The subject may control avatar 832 using a mouse, joystick, or by using gestures or eye tracking. EEG data collected during this task may be labeled based on how the user controls the avatar and the position and movement of the avatar.

Figure 8C:
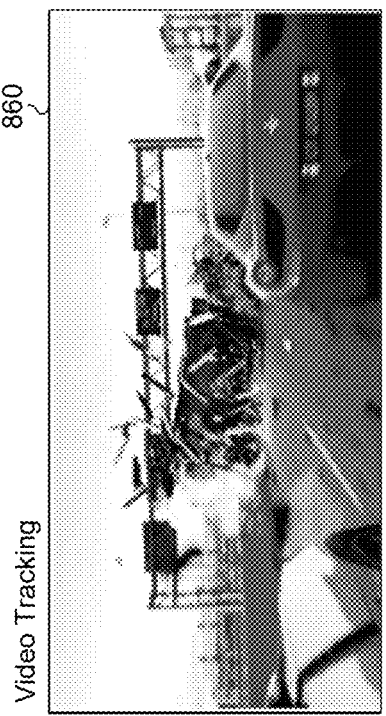

FIG. 8C illustrates a video tracking task 860. During video tracking task 860, a video clip is presented to the subject. The video clip is presented because its visuals, audio, and plot line are rich and varied. The visuals, audio, and plot line can activate the subject's brain in a variety of ways.

Figure 8D:
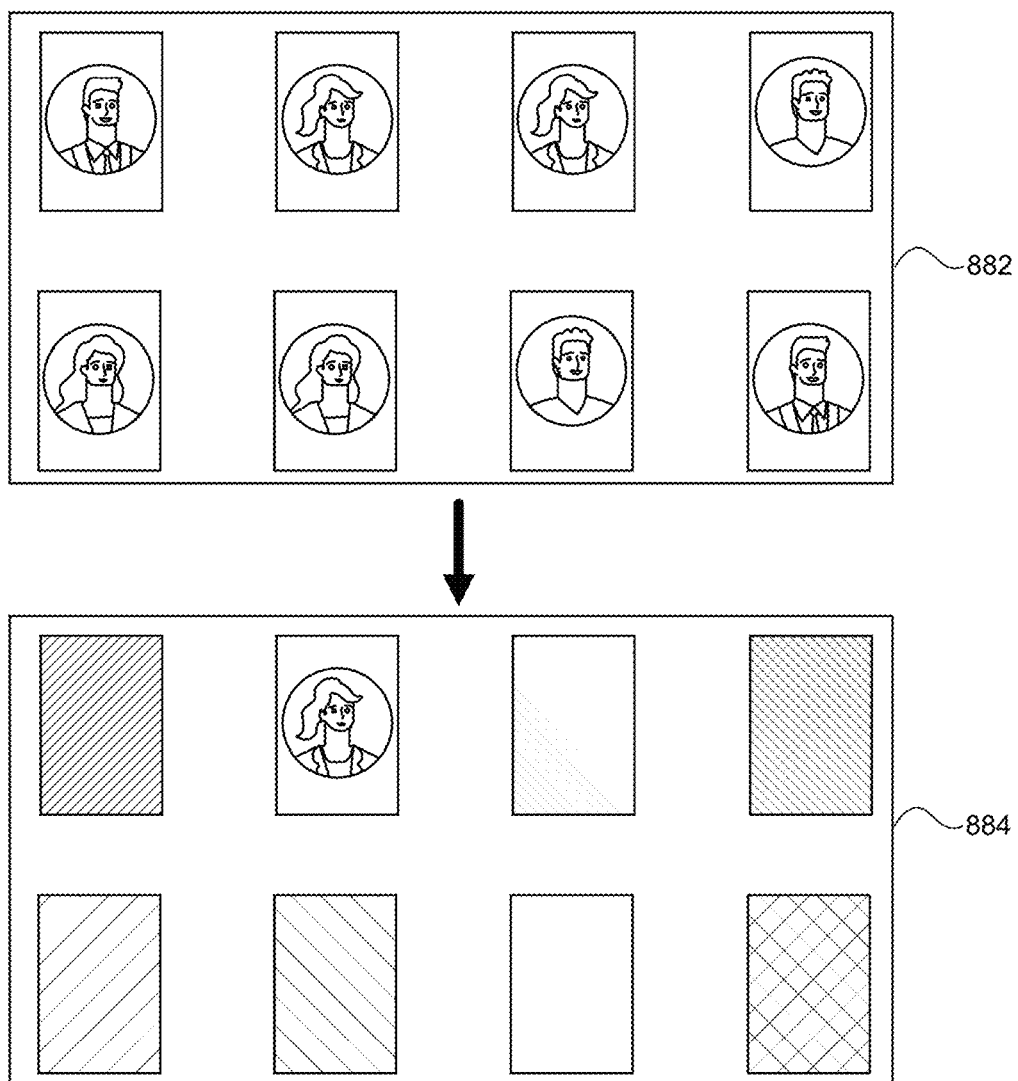

FIG. 8D illustrates a selection task 880. Selection task 880 may involve a classic memory game or another cognitive task. Multiple pairs of identical cards are shown (882) and then flipped over (884), and the user has to select matching pairs of cards, based on their memory. EEG data collected during this task may be labeled based on the intention of selecting each desired card, which in a menu control case can serve for selecting icons or buttons. Additionally, the EEG data collected may be label based on errors versus successful attempts, or based on the content of the card. Such a memory game may create rich dynamics of neural activity involving multiple different functional parts of the brain. The game itself may include visual and auditory stimuli and have perceptual, memory, motor planning, and motor execution aspects to it.

In this way, data from EEG sensors and corresponding labels are collected and stored during training in steps 602 and 604. Additionally or alternatively, time series data from eye tracking and hand tracking devices may also be collected and stored for training. Eye tracking devices can indicate what the person is looking at on the screen. Hand tracking devices can track the position and gesture of the subject's hands using computer vision or other technology. For example, with a selection task, the person may be looking at an item on the screen, the eye-tracker may be used as an input device that selects that item via gaze dwelling time, leading to the next step of the task. During that time, EEG data, game events, and eye-tracking data are continuously collected and stored.

At 606, the EEG data as labeled at step 604 is used to train the at least one machine learning model. In one example, to train the model, a back propagation process may be initiated through the neural network. The back propagation may span through the entire network.

Take for example the network shown in FIG. 5. Starting with the error between the decoder output $\hat{Z}$ and the true labels Z, the back propagation may occur through all elements of neural activity decoded 202 including multi-modal decoder 210, neural activity encoder 208, visual encoder 204, audio encoder 205, subject metadata encoder 306, behavior encoder 308 and calibration neural activity encoder 408. Back propagation may also occur through language encoder 206. In an embodiment, language encoder 206 may be pre-trained using a large language corpus and fine-tuned using the process in FIG. 6.

Back propagation is the process by which the weights to the networks are fitted. In an example, backpropagation computes a gradient of a loss function with respect to the weights of the network. To update the weights, various techniques can be used including gradient descent, or stochastic gradient descent. The weights may be calculated one layer at a time, iterating backward from the last layer using, for example, dynamic programming.

The training process shown in FIG. 6 is repeated for enough training data sets to create a reliable model. Data from many subjects may need to be used to give enough labeled EEG data to reliably infer a neural activity for a new user.

As described above, data collection participants may engage in a number of different types of tasks. The variety of task data may be used to train the network, even though the inference the network may be used to make only relate to one type of task. For example, the training data collected may relate to watching a video or engaging in memory tasks, but the network may ultimately be used to make an inference related to selecting a menu option. Training a network using multiple tasks this way may serve to improve the accuracy of the ultimate inference.

User Calibration of a Neural Decoder

With the model trained, it is ready for use. As described above with respect to FIGS. 4 and 5, a user may need to first calibrate the model to some of the properties of their neural activity patterns that are unique to their own brain. This process is illustrated in FIG. 9.

Figure 9:
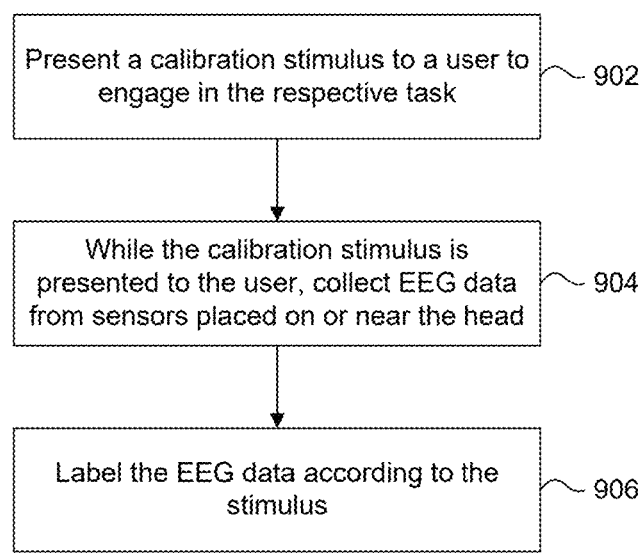
FIG. 9 is a flowchart illustrating a method of collecting EEG data for user calibration.

FIG. 9 is a flowchart illustrating a method 900 of labeling EEG data for user calibration.

At 902, during a calibration process, a calibration stimulus is presented to a user to engage in the respective task. Each calibration stimulus may be presented one or multiple times during the calibration process. The calibration stimulus may include a visual or auditory cue or instructions to perform a particular action. For example, to calibrate for the menu selection task, the calibration stimulus is made to show the different menu options in succession, one at a time. To calibrate for decoding a hand gesture or facial expression task, the calibration task may ask the user to perform the hand gesture or facial expression. In one embodiment, a single stimulus may be presented at a time. This may be advantageous in that it may better control what the user is experiencing and so avoid the ambiguity of a full menu for example. In other embodiments, complex calibration tasks may be used that have multiple, perhaps even competing, stimuli.

In another embodiment, the calibration instruction can refer to the subject's internal ideation. For example, the calibration instruction may ask a person to think of a word or a concept. In one example, a screen may display to the user "home" and then the word disappears. And then the screen may instruct the user, please imagine the word "home" when the tone comes on. And then a few seconds pass, and then there's a beep. That beep is the moment that the subject needs to imagine the concept solicited.

This concept can be used to control a computer program. In this case, the user can think of the word "home" in order to navigate back to the home screen of a computer program. The same idea could be applied to other words, such as "back" to return to a previous screen, and "up," "down," "right," and "left" to navigate within the computer program.

At 904, while the calibration stimulus is presented to the user, first EEG data collected from sensors placed on or near a user's head is received. As mentioned above, the EEG data may be collected from electrodes, as described above with respect to FIGS. 7A-D.

At 906, the EEG data is labeled according to the stimulus. For example, in the menu selection example, the EEG data may be labeled according to the menu option displayed and the position of the menu option on the screen. In an example where there are three menu options, a first set of EEG data is labeled to indicate that a first menu option at a first screen position was being displayed when the EEG data was collected; a second set of EEG data is labeled to indicate that a second menu option at a second screen position was being displayed when the EEG data was collected; and a third set of EEG data is labeled to indicate that a third menu option at a third screen position was being displayed when the EEG data was collected.

As described above with respect to FIG. 5, method 900 may be repeated to ask the user to complete a plurality of different tasks. For example, a resting instruction may be presented, asking the user to rest; a gesture instruction may be presented, asking the user to complete a movement; and a video stimulus may be presented, which the user is instructed to watch.

Each specific type of stimulus can be defined by a set of parameters that describe it. For example, a visual stimulus of a menu item includes the item's shape, size, location on the screen, colors, etc. For another example, an auditory stimulus of a spoken command includes its meaning, the speaker's intonation, perceived location in space where the sound emanated from, etc.

Additionally, each stimulus can be presented with a particular temporal profile. A stimulus can be presented briefly and then hidden. Alternatively, the stimulus may be presented in a periodic fashion, at a specific frequency, or at some particular temporal pattern. For example, a menu option may be presented and hidden repeatedly at the frequency. When hidden, the portion of the screen previously occupied by the stimulus may be black. The temporal profile of the stimulus should cause any flickering to be imperceptible or nearly imperceptible to the subject. For a visual stimulus for example, the neural response to a brief visual stimulus is commonly called a Visual Evoked Potential. The neural response to a visual stimulus that is presented in a periodic fashion is commonly called a Steady-State Visual Evoked Potential.

Figure 10:
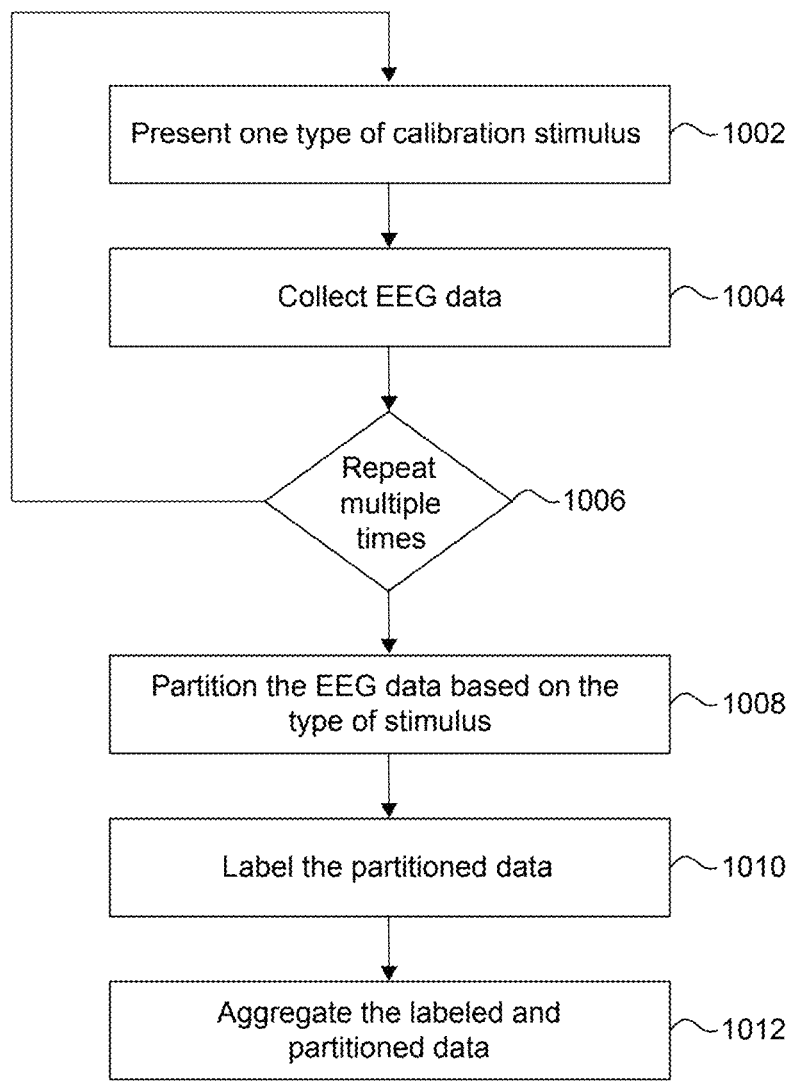
FIG. 10 is a flowchart illustrating a method of aggregating EEG data for user calibration.

During the calibration process, EEG data can be aggregated based on any of the stimulus parameters, as described above. This is illustrated in FIG. 10, which is a flowchart of a method 1000 of aggregating EEG data collected during calibration.

Method 1000 begins at step 1002 when one type of calibration stimulus or instruction is presented to a user. At 1004, while the calibration stimulus or instruction is presented to the user, EEG data collected from sensors attached to a user's head is received. As described above, each stimulus type may be presented in a specific temporal profile. At 1006, steps 1002 and 1004 are repeated for the same or a different stimulus type or instruction.

At 1008, the EEG data is partitioned into segments each related to one stimulus presentation. If the stimulus presentation's temporal pattern was periodic, the EEG data from each presentation can be further partitioned based on the period of the temporal profile. Turning to diagram 1100 in FIG. 11, graph 1104 shows a single activation and deactivation of the stimulus. While graph 1104 illustrates the activation-deactivation cycle as a square wave, it may fade in and out, such as in a sine wave pattern or another more complex temporal pattern.

As mentioned above, this temporal pattern may repeat periodically. EEG data 1102A-C each represents EEG data collected from a single EEG sensor during one cycle. In other words, together EEG data 1102A-C presents data collected from an EEG sensor over the course of three activation-deactivation cycle. In this example, the EEG data collected from the single EEG sensor is partitioned into segments. For example, suppose a menu option appears and disappears 100 times during each stimulus presentation. In that example, the EEG data from that stimulus presentation is partitioned into 100 segments.

Returning to FIG. 10 at 1010, the partitioned data labeled and sorted based on one of the calibration stimulus or instruction properties as described above. As mentioned above, the properties of a visual stimuli, for example, can include its visual characteristics, e.g., item's shape, size, location on the screen, colors, and its temporal profile. This results in a set of segments related to a specific property of a stimulus or instruction type. Continuing the first example above, suppose 100 EEG segments are collected, each representing an appearance-disappearance of one type of menu option presented.

Figure 11:
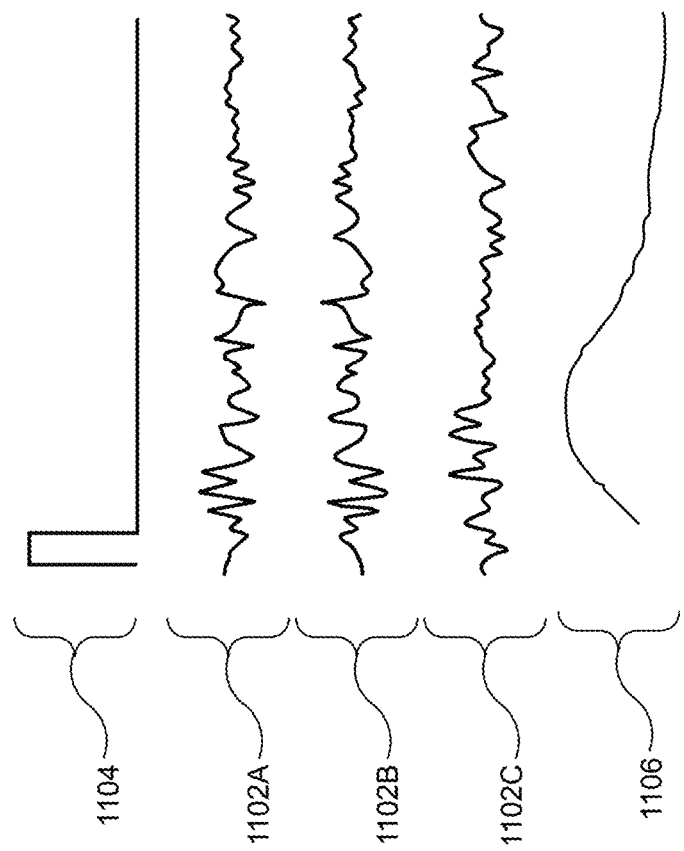
FIG. 11 is a chart illustrating a result of modeling and aggregating various segments of EEG data.
Figure 12:
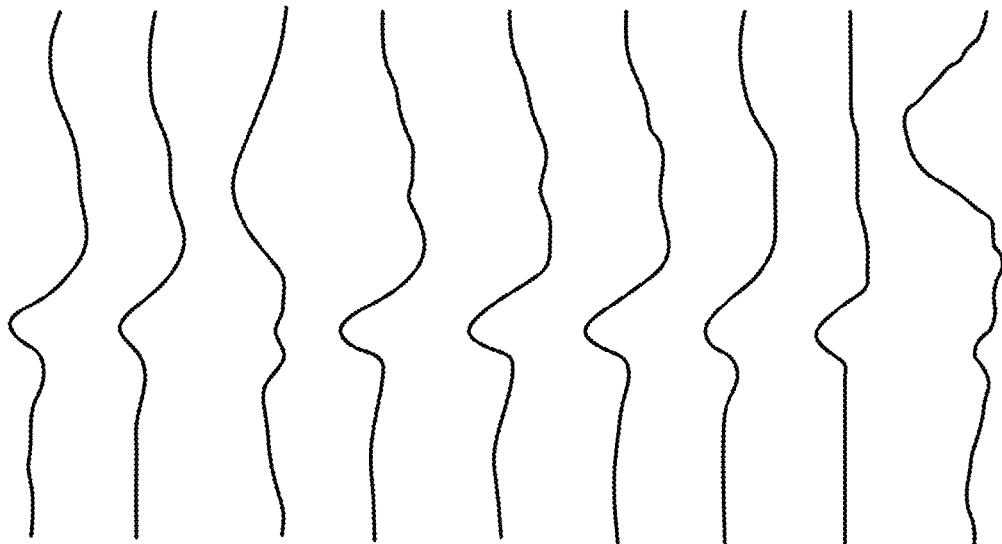
FIG. 12 is a chart illustrating examples of different patterns of aggregated segments of EEG data collected from different electrodes.

At 1012, optionally, the EEG segments each stimulus or instruction property is aggregated. Aggregation can be performed in multiple ways. For example, at each time point, a mean and standard deviation of the voltage information is determined. Continuing the first example above, suppose 100 EEG segments are collected, each representing appearance-disappearance of a menu option. This results in an aggregated curve as illustrated in FIG. 11 by line 1106. This aggregated data may be the neural data (404 in FIGS. 4, and 504A-C in FIG. 5) fed out of the user calibration module (410 in FIGS. 4, and 510A-C in FIG. 5) and into the neural encoder (406 in FIGS. 4, and 506A-C in FIG. 5).

The aggregation in step 1012 is optional. Alternatively, user calibration module (410 in FIGS. 4, and 510A-C in FIG. 5) could be fed by the set of actual segments of EEG data themselves.

In an embodiment, multiple EEG sensors may be touching or near the user's head. A set of aggregated, partitioned, labeled EEG data is determined for each EEG sensor. As shown in diagram 1200 in FIG. 12, in an embodiment there may be nine EEG sensors resulting in nine aggregated, partitioned, labeled EEG time series, forming a set of calibration data. Each of these time series are input into neural activity encoder 408 in user calibration module 410 in FIG. 4. In the menu selection example, a set of (optionally) aggregated, partitioned, and labeled calibration data may be determined for each available menu option.

As described above for FIG. 5, multiple calibration stimuli may be applied to collect data under multiple different circumstances, with the user performing multiple different tasks, such as menu selection, movement, resting, and ideation.

In this way, a template ground truth is generated. This template ground truth can be used to infer neural activity using deep template matching. Every time that a stimuli is viewed, measured EEG data can be compared with the template to determine whether it follows a similar pattern. How an inference is made is described below with respect to FIG. 13.

Multi-modal Inference of a Neural Decoder

Figure 13:
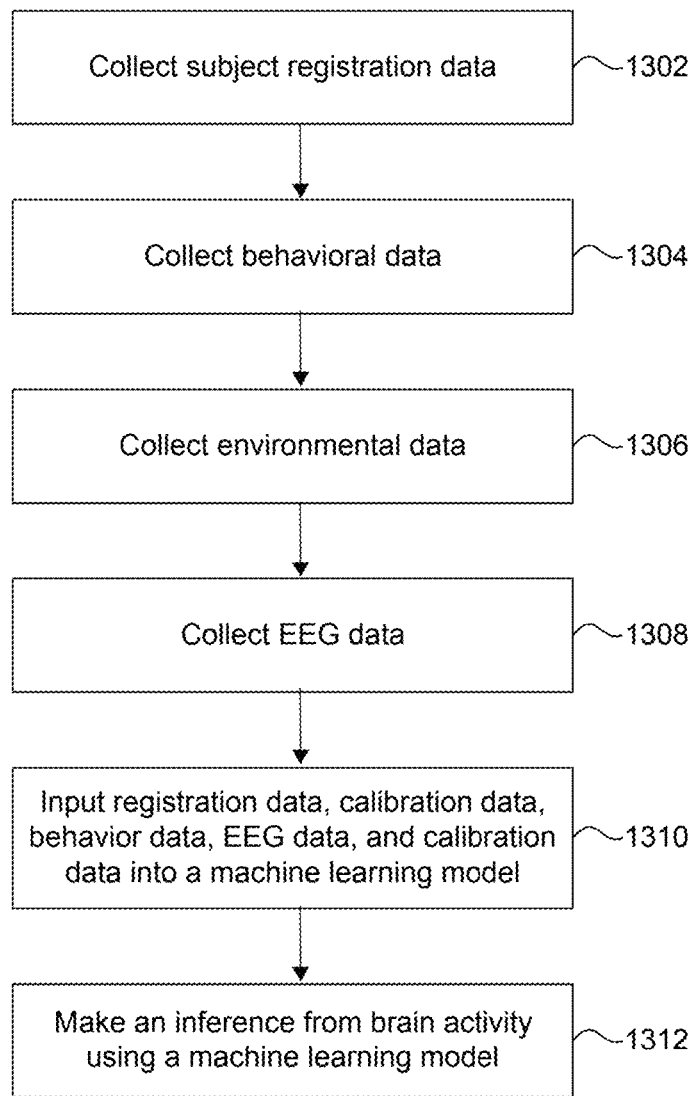
FIG. 13 is a flowchart illustrating a method of neural decoding.

FIG. 13 is a flowchart illustrating a method of neural decoding 1300, according to an example.

At 1302, registration data describing information about the user is received. The registration data may have been self-reported by the user during registration of an account for the user. For example, the registration data may include the subject's biological gender (e.g., male or female), the subject's birthdate (and hence age), the subject's handedness (right-handed or left-handed), the subject's genetic sequencing, and subject's multiomics data.

At 1304, behavior data describing what the user is doing is measured. The behavior data may describe what the user is doing concurrently with measurement of the EEG data. The behavior data may include movement data (for example, measured from an inertial measurement unit on the headset), hand gesture data, and eye tracking data. In another example, the subject's health data measured from other wearable devices may be used. This health data may include data describing the subject's heartrate, electrocardiogram, and blood oxygen level.

At 1306, environmental data describing stimulus the user is exposed to is received. The environmental data may be what the user is exposed to concurrently with the measurement of the EEG data. In an embodiment, the environmental data describes what the user is seeing concurrently with the measurement of the EEG data. For example, environmental data may include what is currently being displayed to the user by an operating system or other computer program and what is captured in a camera on an augmented or mixed reality device.

Additionally or alternatively, the environmental data may comprise audio data that describes what the user is hearing concurrently with the EEG data. The audio data may be what is currently being played by an operating system or other software program on the device, or may be captured from a microphone. As described above, the environmental data can include language data as well.

Figure 14:
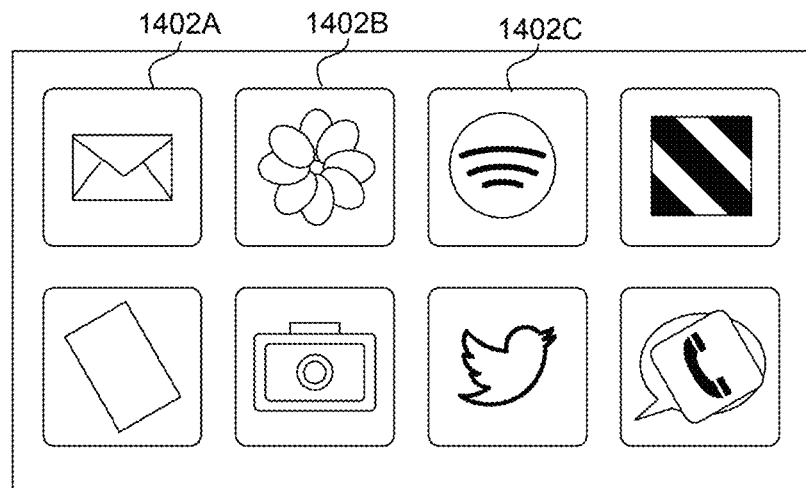
FIG. 14 is an example of a display that contains options for users to select.

An example of the environmental data is illustrated in FIG. 14. In particular, FIG. 14 is an example of a display 1400 that contains a menu with options for users to select. For example, the menu includes options 1402A, 1402B, and 1402C. When selected, the computer program will take different actions depending on the option selected.

Figure 15:
FIG. 15 is a chart illustrating how environmental data can be flickered on and off to stimulate neural activity.

Additionally or alternatively, different visual stimuli, such as the menu options in FIG. 14, may be presented with a different temporal profile. For example, as shown by chart 1500 in FIG. 15, an option such as option 1402A may repeatedly appear and disappear. This activation-deactivation cycle may be so fast that it may be imperceptible to a user. Options 1402A, 1402B, and 1402C may each activate and deactivate at a different frequency, one may activate-deactivate at 50 Hz, another at 40 Hz, etc., or at a different phase. As mentioned above, the activate-deactivate cycle may be a square wave with the option appearing and disappearing, it may include fading the option in and out, as in a sine wave, or another more complex temporal profile. The temporal profile here may be applied as described above with respect to user calibration.

Figure 16:
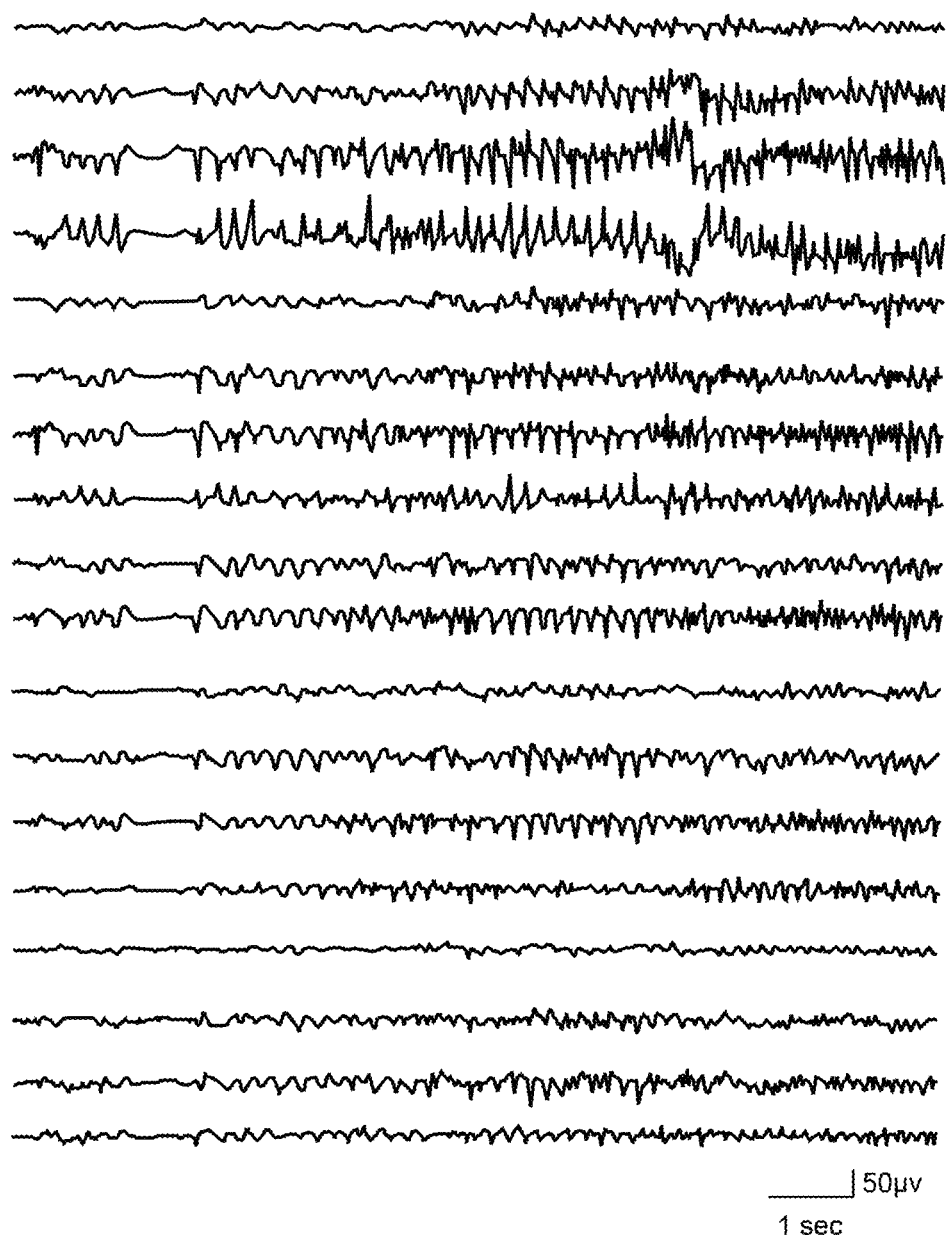
FIG. 16 is a chart illustrating an example of EEG data collected from a plurality of electrodes.

At 1308, EEG data collected from sensors attached to or near a user's head is received. As mentioned above, the EEG data may include a plurality of time series of voltage information, each collected from a different EEG electrode touching a different position of the user's head. FIG. 16 is a chart 1600 illustrating an example of EEG data collected from the plurality of different sensors.

At 1310, the registration data, the behavior data, the environmental data, the EEG data received at step 1308, and the EEG data collected during calibration as described above with respect to FIGS. 4 and 5 are all input into at least one machine learning model trained to determine an inference related to neural activity. As described above with respect to FIGS. 2-5, the machine learning model is trained using a training data set of additional EEG and additional concurrently collected environmental data collected from data collection participants. The machine learning model may include a neural activity encoder for the EEG data measured at step 1308, audio and visual encoders for the environmental data measured at step 1306, a behavior data encoder for the behavior data measured at step 1304, a metadata encoder for the subject registration data measured at step 1302, a neural activity encoder for the calibration data, and a multi-modal decoder.

At 1312, the machine learning model is used to determine an inference related to neural activity. In one embodiment, the inference may be whether the user intends to select from a menu of options and which of the options to select. Upon making the inference, the selection may be used to control the computer program. In another embodiment, the inference may be that the user intends to make or is making a movement, such as a facial expression or hand gesture. In the third embodiment, the inference may be the user's identity. Determining the user's identity is also described below with respect to FIG. 17.

In an embodiment where the machine learning model is a deep learning network, inference may be made using a feed forward functionality of the deep learning network. The deep learning network may include a plurality of node layers, including an input layer, one or more hidden layers, and at least one output layer. Nodes from each layer connect to some or all nodes from the next layer and this connection has an associated weight. The resulting activation is then pass through a nonlinear function, for example the rectified linear (Relu) function. The weights and other meta-parameters of the network may be set using the back propagation process described above with respect to FIG. 6. During inference, data is input into the input layers, values are propagated forward through the network via the series of computations defined by the network architecture described above, and the network ultimately makes an inference at the output layer. A skilled artisan would understand that many network architectures and training schemes are available to train and provide an inference in this way.

Authentication Using EEG Data

Figure 17:
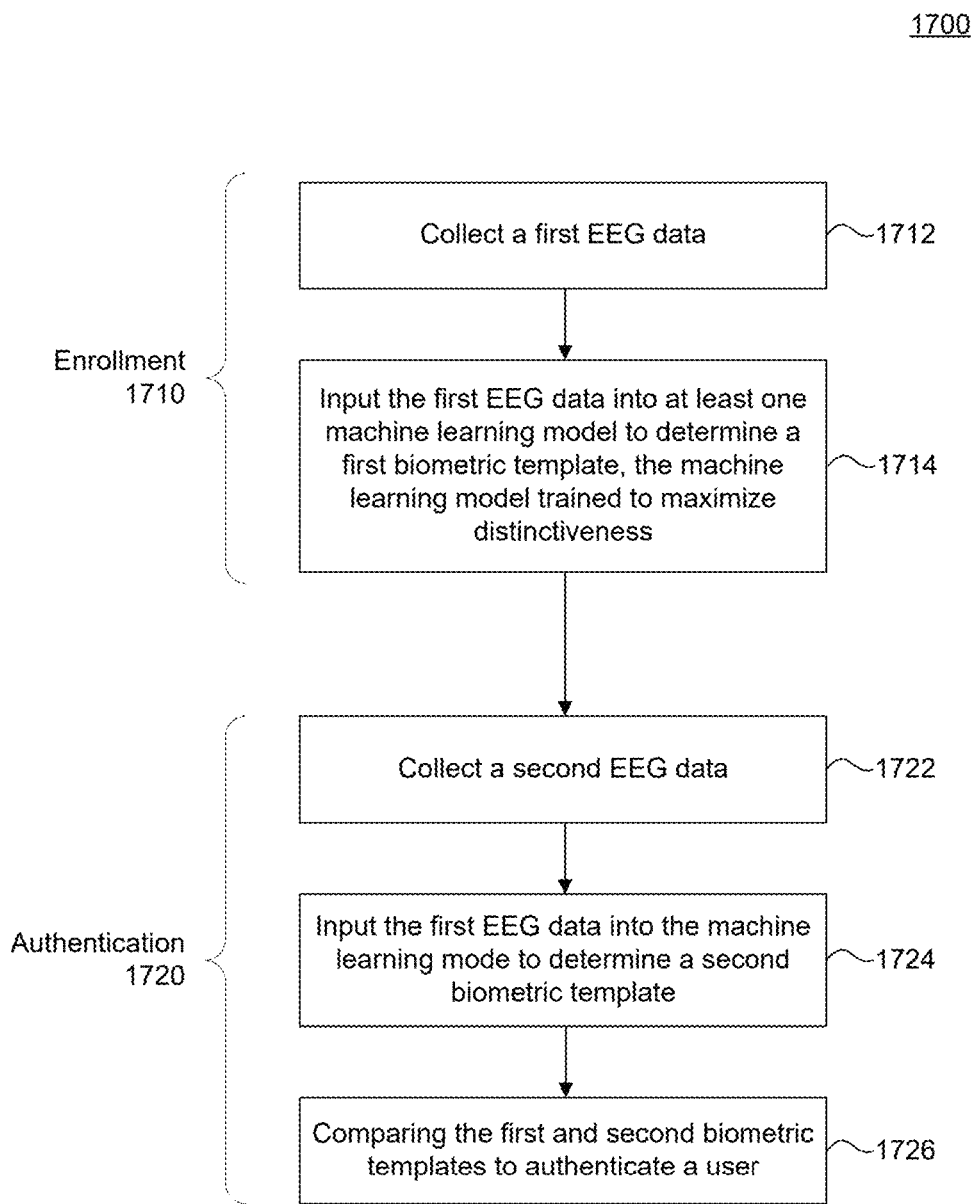
FIG. 17 is a flowchart illustrating a method of identifying a user by comparing two biometric templates that are determined by a machine learning model using neural data.

FIG. 17 is a flowchart illustrating a method 1700 of identifying a user by comparing at least two biometric templates that are determined by a machine learning model to authenticate a user.

Method 1700 is divided into two phases—an enrollment phase 1710 and an authentication phase 1720. Similar to the calibration discussed with respect to FIGS. 4, 5, and 9, enrollment phase 1710 may occur, for example, when the user is first setting up their account. Enrollment phase 1710 includes two steps-step 1712 and step 1714.

At 1712, EEG data collected from sensors attached to or near a user's head is received. The electroencephalogram (EEG) data may include a plurality of different time segments (say, 1-2 second intervals) and may include data simultaneously collected from a plurality of electrodes. The user may be at rest, and a stimulus may be provided to the user instructing the user to remain at rest. In another embodiment, the user may be presented with a visual or auditory stimuli the user needs to attend to.

During 1712, the user may be asked to engage in a variety of different tasks. For example, it may ask the user to relax, to open their eyes, to close their eyes, to gaze at a visual stimuli, to move, etc. Having a variety of tasks during enrollment may help the model ignore the tasks performed and focus on identifying the individual performing them.

At 1714, the first EEG data is input into at least one machine learning model to determine a biometric template related to neural activity. The machine learning model has been previously trained using a training data set of additional EEG data from data collection participants to maximize distinctiveness. The loss function used during training is selected to maximize distinctiveness between participants regardless of their current task. The machine learning model may be trained to differentiate between different people. As a result, the machine learning model may cluster different people in different locations in a space of all possible outputs from the model. Each individual has different data points, for example, in the form of different time segments of EEG data. These data points for one individual may form one cluster.

Figure 18:
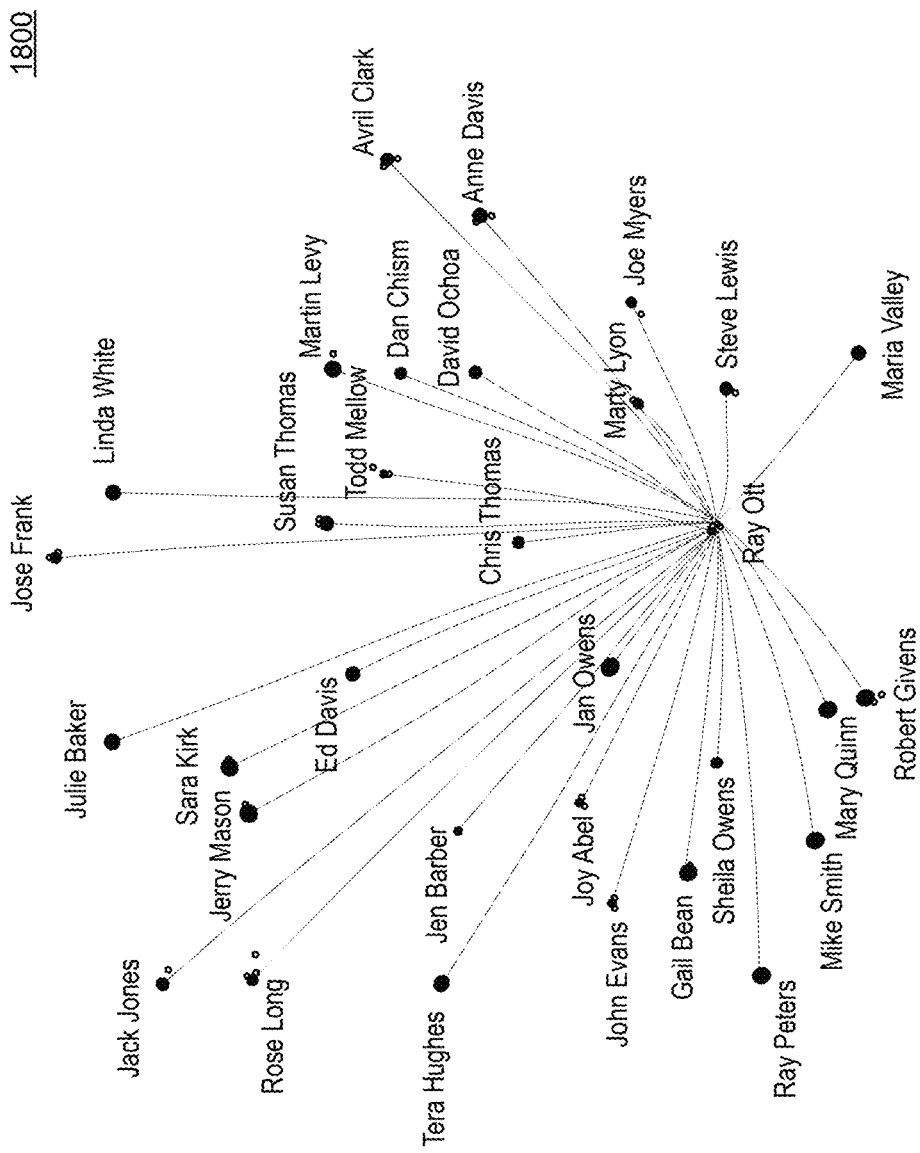
FIG. 18 is a diagram illustrating distinctiveness of biometric templates that are determined by a machine learning model.

The brain biometric template may be a number or a series of numbers creating a vector. FIG. 18 shows a diagram 1800 illustrating a plurality of biometric templates that are determined by a machine learning model. Diagram 1800 plots each biometric template in three dimensional space for illustrative purposes, but in practice each vector may have many dimensions.

Returning to FIG. 17, authentication phase 1720 may occur at login. It may also periodically or continuously occur while the user is using the device. For example, whenever the user is at rest, authentication phase 1720 may re-authenticate the user. When the user takes the device off or if another user places the device on, authentication may fail and the device may lock.

Authentication phase 1720 includes three steps-steps 1722, 1724, and 1726.

At 1722, EEG data measured from sensors attached to or near a user's head is received. Again, the EEG data measured may be measured as described above with respect to FIGS. 7A-B.

At 1724, the EEG data received at step 1722 is input into the machine learning model used at step 1714 to determine a biometric template related to the user's neural activity.

At 1726, the biometric template determined at step 1714 is compared to the biometric template determined at step 1724 to determine the user's identity. To determine the user's identity, a distance between the first and second biometric templates is calculated. The distance may be a Euclidian distance between the two vectors. If the distance is below a threshold, the user's identify is authenticated.

In one embodiment, the user may have, for example, already identified themselves (such as through a username) and step 1726 verifies the user's identity. In another embodiment, the user need not have previously identified themselves. For example, when the user puts on a headset, steps 1722-1726 are initiated automatically and, at step 1726, the biometric template determined at step 1722 is evaluated against a database of biometric templates representing all known users of the system. The biometric template in the database closest to the value determined at step 1724 is evaluated. If the distance between the biometric template determined in 1724 and the next closest in the database is below a threshold, the user is identified.

Figure 19:
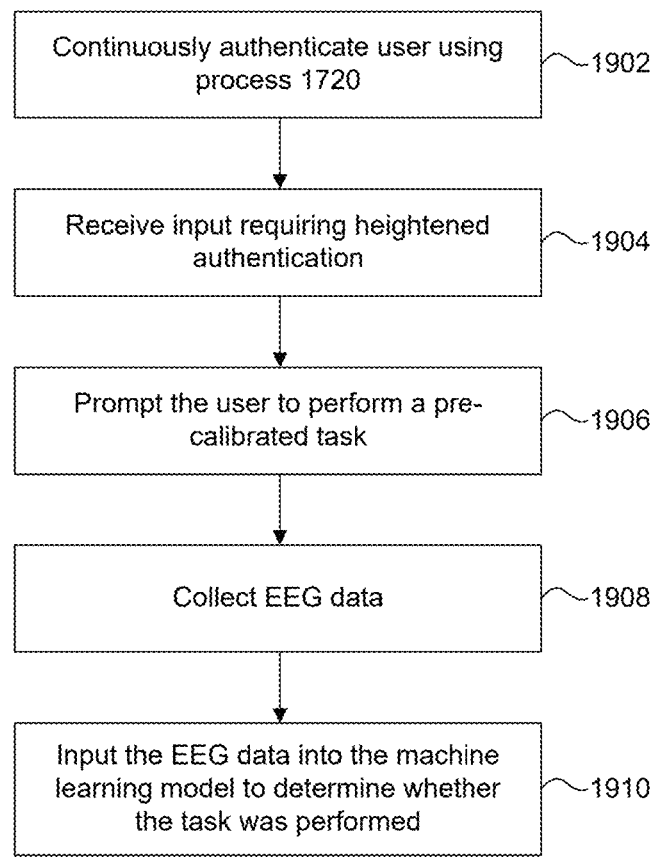
FIG. 19 is a flowchart illustrating a method of multi-factor authentication.

FIG. 19 is a flowchart illustrating a method 1900 of multi-factor authentication, according to an example. In an example, the three factors may be "something you have" (e.g., the device), "something you are" (e.g., represented by a biometric template) and "something you know" (e.g., decoding an ideated password).

At 1902, the authentication phase 1720 is continuously repeated. Authentication phase 1720 may be continuously verifying the user based on the user's brain biometric template. In this way, the authentication occurs based on "something you are." For example, the user may be wearing a headset. Whenever the user is wearing the headset (and perhaps in a resting state), authentication phase 1720 is repeated to verify that the user is still wearing the headset and no other user has logged in. When the authentication fails (e.g., when the user wearing the headset is not who is logged in), the headset may be locked to prevent access to applications or data.

At 1904, an input to conduct an activity on the headset requiring heightened authentication is received. In embodiments, the activity may involve accessing sensitive data or logging in to an application with sensitive privileges. For example, when the user of the headset may be accessing a banking or other financial services application. These functions may require a second authentication factor to verify the user's identify.

At 1906, the user is prompted to perform an ideation task for further authentication. For example, the user may be prompted to imagine a specific color or think of a specific word. Underlying the correct ideation is a unique neural activity pattern that allows further verification of based on "something you know."

At 1908, while the user is performing the task for further authentication, EEG data measured from the sensors is received.

At 1910, the EEG data is input into a machine learning model to determine whether it is similar to EEG data collected during a calibration process. The machine learning model may be different from the one used to determine the user's identity in the first instance in step 1726. Similar to what was described above with respect to FIGS. 4, 5, and 9, the machine learning model in 1910 may need to be calibrated to the specific user.

In an embodiment, during an enrollment process, a calibration stimulus is presented to a user to engage in a calibration task. For example, the user may be prompted to imagine a specific color or think of a specific word. When the calibration stimulus is presented to the user, EEG data collected from the sensors is received. The EEG data is input into a machine learning model to determine a biometric template for the multi-factor authentication. The machine learning model has been previously trained using a training data set of additional EEG data from data collection participants to maximize distinctiveness of the data collection participants performing the calibration task, for example, imagining different colors or thinking of different words.

In that embodiment, when the third authentication factor is required of the user, the user is prompted to again perform a short task similar to the calibration task for further authentication. While the user is performing the calibration task for further authentication, additional EEG data is collected from the sensors and input into the machine learning model to determine another biometric template related to neural activity. The biometric template is compared to the one generated while performing the calibration. For example, a distance between the two signatures is determined, and, based on the distance, the heightened authentication verified. This may allow the user to engage in more sensitive and privileged functionality in the process.

Classifying a Brain Profile Using a General Representation

Figure 20:
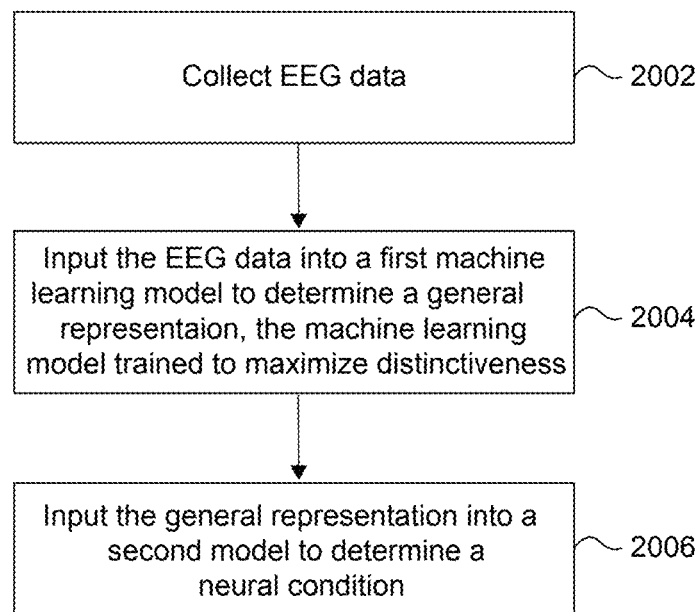
FIG. 20 is a flowchart illustrating a method of determining a brain profile using EEG data.

FIG. 20 is a flowchart illustrating a method 2000 of determining a brain profile using EEG data. A brain profile may be thought of as clustering of identities based on biometric templates that are related to some property of the users. For the purpose of brain profiling, a machine learning model may learn a general representation for each user, which is conceptually similar to the biometric templates described above. These general representations aim to capture as much information about the user's neural activity that will enable decoding of multiple profiles. The property that defines a brain profile may be a condition relating to the subject's health, such as a brain disorder or a psychiatric disease. Such abnormalities may include major depression, schizophrenia, ADHD or autism. In this way, decoding a brain disorder can be useful in the context of drug discovery or as a tool for clinicians. In the healthcare context, this is sometimes referred to as a digital biomarker. A brain profile may also signify a subject's propensity for learning a particular subject matter or skill, such as successful completion of flight school. This may be useful for screening people for their job roles in a military or academic setting.

At 2002, EEG data collected from sensors attached to or near a user's head is received. In one embodiment, the EEG data may be collected using the consumer devices illustrated in FIGS. 7A-D. In another example, the EEG data may be collected using research grade EEG headsets discussed above with respect to step 602 in the training method in FIG. 6.

As described above with respect to FIGS. 4 and 5, the user can be exposed to one or more stimuli as described with respect to user calibration modules 410 and 510A-C. In an example, the stimuli may include complex, rich games. It can use visual and auditory stimuli to evoke diverse neural activity that is expected to differ between users having different brain profiles. The stimulus may be repeating and the EEG data may be segmented, aggregated (optionally), and labeled, as described above with respect to FIGS. 10-12.

In addition to EEG data, behavior data may be collected. The behavior data may include, for example, eye trackers or hand trackers. As described above with respect to FIG. 5, EEG data, along with labels, behavior data, and subject metadata may be input into a machine learning algorithm in step 2004.

At 2004, the EEG and other data received at 2002 is input into a first machine learning model to determine a general representation related to neural activity. The first machine learning model was previously trained using a training data set of additional EEG data from data collection participants. The first machine learning model may be a deep learning neural network whose architecture resembles that used for calibration. And, as a result, the general representation is conceptually similar to $f_7(X_N, Z_N)$ of FIG. 5.

At 2006, the general representation determined at 2004 is input into a second machine learning model. The second machine learning model was previously trained with general representations and a label indicating the brain profiles of the respective data collection participants. The second machine learning model outputs whether the user has the brain profile or not, or to what extent the user has the brain profile. The second machine learning model uses a classification algorithm trained from the plurality of subjects. Such subjects from the plurality of subjects are classified according to their brain profiles. The second machine learning model may be a deep learning neural network. In this way, the general representation can be used to determine whether the user has a specific brain profile.

Method 2000 need not be executed in real time. All available data collected from a user during one or more entire recording sessions (e.g., 1 hr) could be used, and the user's brain profile based on features extracted from all of this given data. This is in contrast to the menu selection user-case where the decoding, relies on calibration data, but makes the prediction based on a given and single EEG segment.

Additionally or alternatively, different models may be used in step 2006 to assess, using the general representation, whether a user has a specific brain profile. For example, one model may be trained to determine, based on the general representation, whether a user has major depression, while another model may be trained to determine, based on the general representation, whether a user has autism.

System Components

FIG. 21 is a diagram illustrating a computing device 2100 used on the head mounted device, according to an example. In this example, computing device 2100 contains an EEG sensor 2104, a visual unit 2110, an audio unit 2116, a motion detection unit 2124, a communication unit 2126, and a processor 2122, all communicatively connected via bus 2128.

EEG sensor 2104 may contain a single or multiple non-invasive EEG electrodes that can be used to collect and record biosignals (i.e. EEG data).

Visual unit 2110 may comprise a display 2112 and an image detector 2114. Display 2112 may be a digital screen that shows multimedia features to a user using one or more display technologies (e.g. LCD, OLED, etc.). Display 2112 may be curved or flat, and it may be a whole piece or split pieces. Image detector 2114 may be digital cameras or other light sensor modules that can detect the user's eye movement and record the movement. The digital cameras or other light sensor modules in image detector 2114 may also monitor objects around the head mounted device and detect when an object is too close to the head mounted device.

Audio unit 2116 may comprise a speaker 2118 and a microphone 2120. Speaker 2118 may be an electroacoustic transducer that converts an electrical audio signal into a corresponding sound. Speaker 2118 may be a system that can play multiple sound tracks simultaneously. Microphone 2120 may be a transducer that converts sound into an electrical signal. Microphone 2120 may contain noise-cancelling techniques that can reduce noise inferences in the electrical signal.

Motion detection unit 2124 may be an electrical device that utilizes a sensor to detect nearby motion. Motion detection unit 2124 may contain digital cameras or other light sensor modules that can precisely locate the user's limbs and record the movement of the limbs. It may include for example an inertial momentum unit.

Communication unit 2126 may contain a transmitter and a receiver. The transmitter may be an electronic device which produces radio waves with an antenna. The transmitter can generate a radio frequency alternating current and apply this current to the antenna. The receiver may be an electronic device that uses an antenna to receive radio waves and converts the information carried by them to a usable form.

Processor 2122 may be an electronic circuitry that executes instructions comprising a program. Processor 2122 may perform basic arithmetic, logic, controlling, and input/output (I/O) operations specified by the instructions in the program. Processor 2122 may also contain a memory (e.g. a memory disk, a RAM, etc.) that can store digital data in it, including the instructions to execute the various methods described above.

For an example program, computing device 2100 may start to run when motion of the user's limbs is detected by motion detection unit 2124. Computing device 2100 may also start when image detector 2114 detects a specific eye movement of the user. Computing device 2100 can also start when microphone 2120 records a specific vocal word or phrase.

When computing device 2100 starts, processor 2122 may first instruct display 2112 and speaker 2118 to play multimedia contents according to the example program. Processor 2122 may also activate EEG sensor 2104, image detector 2114, microphone 2120, and motion detection unit 2124 and instruct them to transmit the data they have recorded to the memory in processor 2122.

After receiving the recorded data, processor 2122 may track the data from the memory, reorganize, pack, compress, and/or encrypt the data. Processor 2122 may send the data together with the program information to communication unit 2126. Processor 2122 may then instruct communication unit 2126 to transmit this local data (i.e. the data that has been processed by processor 2122) to a cloud system via the transmitter. This process may be performed periodically or continuously.

The receiver in communication unit 2126, accordingly, may periodically or continuously receive cloud data (e.g. computing result, update request, etc.) from the cloud system and send the cloud data to the memory in processor 2122. Processor 2122 may process the cloud data and execute further instructions of the program with the cloud data.

Figure 22:
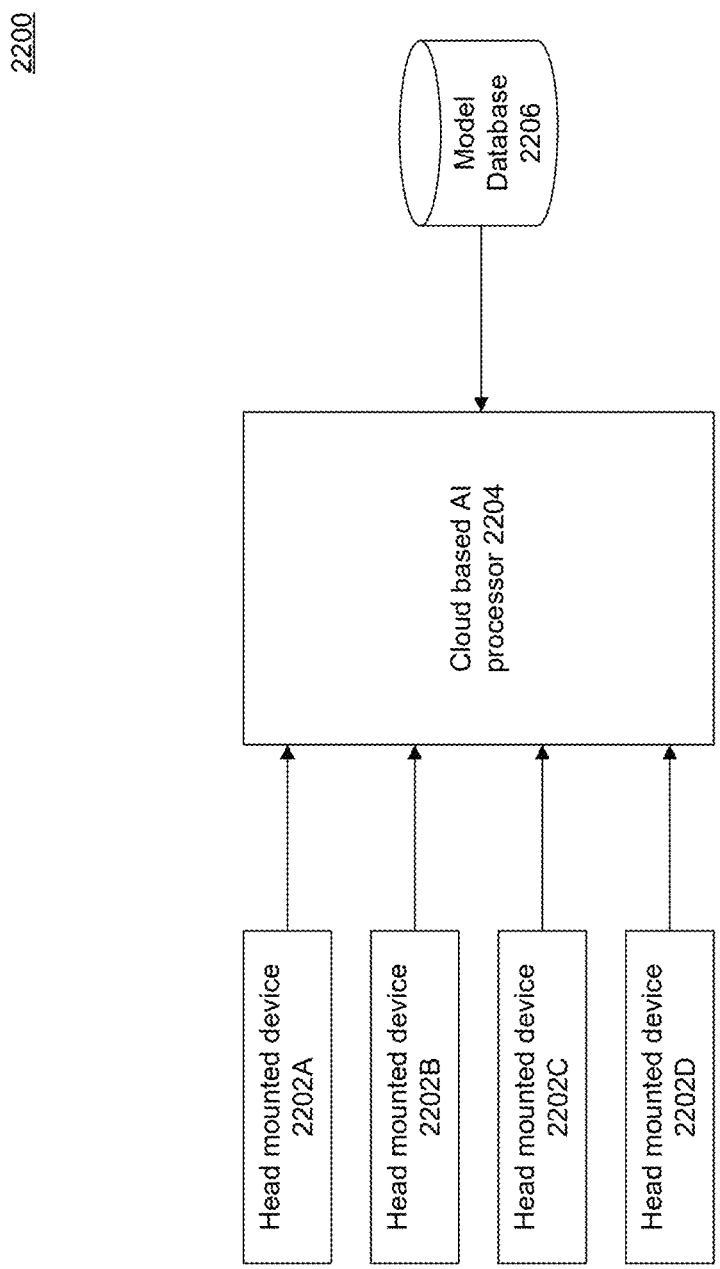
FIG. 22 is a diagram illustrating an example of a system that connects a head mounted device and a server with access previously trained models.

FIG. 22 is a diagram illustrating an example of a system 2200 that connects a head mounted device and a server with access to model data. In this example, system 2200 contains multiple head mounted devices 2002A-D, a cloud based AI processor 2204, and a model database 2206.

Each head mounted device 2002A-D may contain a computing device, as described above with respect to FIG. 21. The computing device may contain a communication unit. The communication unit can transmit and receive data from the cloud based AI processor. A head mounted device may transmit or receive data from the cloud based AI processor when the computing device in the head mounted device instructs the communication unit to do so.

Model database 2206 may be an organized collection of model data that can be stored and accessed electronically. Model data may be data that has been collected and processed previously and selected to be a model, it may also be data that has been created as a standard. In preferred embodiments, model data may be clean data without environmental inferences. Model database can also transmit and receive data from cloud based AI processor. The model database may communicate with the cloud based AI processor when it receives a request from the cloud based AI processor.

The cloud based AI processor 2204 may be a machine learning system that is used to decode information from data which is received from the head mounted devices. The cloud based AI processor may use model data received from the model database as a reference to eliminate environmental inferences in data that is received from the head mounted devices. The cloud based AI processor may also train itself using both data received from the head mounted devices and from the model database. When multiple head mounted devices transmit data to the cloud based AI processor, the cloud based AI processor may process the data simultaneously or according to a schedule.

The above detailed description and embodiments of the disclosed system are not intended to be exhaustive or to limit the disclosed system to the precise form disclosed above. While specific examples for the system are described above for illustrative purposes, various equivalent modifications are possible within the scope of the disclosed system, as those skilled in the relevant art will recognize. For example, while processes and methods are presented in a given order, alternative implementations may perform routines having steps, or employ systems having processes or methods, in a different order, and some processes or methods may be deleted, moved, added, subdivided, combined, or modified to provide alternative or sub-combinations. Each of these processes or methods may be implemented in a variety of different ways. Also, while processes or methods are at times shown as being performed in series, these processes or blocks may instead be performed or implemented in parallel, or may be performed at different times.

Identifiers, such as "(a)," "(b)," "(i)," "(ii)," etc., are sometimes used for different elements or steps. These identifiers are used for clarity and do not necessarily designate an order for the elements or steps.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such as specific embodiments, without undue experimentation, and without departing from the general concept of the present invention. Therefore, such adaptations and modifications are intended to be within the meaning and range of equivalents of the disclosed embodiments based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. A computer-implemented method for authenticating a user, comprising:
   during enrollment:
   (a) receiving a first electroencephalogram (EEG) data collected from a headset comprising sensors attached to or near the user's head;
   (b) inputting the first EEG data into a first machine learning model to determine a first biometric template related to neural activity, the first machine learning model trained using a first training data set of additional EEG data from data collection participants to maximize distinctiveness;
(c) when an enrollment stimulus or instruction is presented to the user to engage in a calibration task, receiving a second EEG data collected from the sensors;
(d) inputting the second EEG data into a second machine learning model to determine a second biometric template related to neural activity, the second machine learning model trained using a second training data set of additional EEG data from the data collection participants performing the calibration task;
repeatedly while the user is wearing the headset:
(e) receiving a third EEG data measured from the sensors of the headset;
(f) inputting the third EEG data into the first machine learning model to determine a third biometric template related to the neural activity;
(g) comparing the first and third biometric templates to determine the user's identity;
(h) when the comparing (g) determines the user wearing the headset is not who is logged in, locking the headset;
(i) receiving an input to conduct an activity on the headset requiring heightened authentication; and
(j) in response to a requirement for an additional authentication factor to verify the user's identity, comparing the second and third biometric templates to authenticate the user's identity.

2. The computer-implemented method of claim 1, wherein the first and second machine learning models comprise a deep learning neural network.

3. The computer-implemented method of claim 1, wherein the comparing (g) comprises:
determining a distance between the first and third biometric templates; and
authenticating the user based on the distance.

4. The computer-implemented method of claim 1, wherein the requirement for the additional authentication factor comprises:
presenting at least a portion of the enrollment stimulus or instruction to challenge the user for further authentication;
when the user is challenged, receiving a fourth EEG data collected from the sensors;
inputting the fourth EEG data into the second machine learning model to determine a fourth biometric template related to the neural activity; and
comparing the second and fourth biometric templates to further verify the user's identity.

5. A non-transitory, tangible computer-readable device having instructions stored thereon that, when executed by at least one computing device, cause the at least one computing device to perform operations for authenticating a user, the operations comprising:
during enrollment:
(a) receiving a first electroencephalogram (EEG) data collected from a headset comprising sensors attached to or near the user's head;
(b) inputting the first EEG data into at least one a first machine learning model to determine a first biometric template related to neural activity, the first at least one machine learning model trained using a first training data set of additional EEG data from data collection participants to maximize distinctiveness;
(c) when an enrollment stimulus or instruction is presented to the user to engage in a calibration task, receiving a second EEG data collected from the sensors;
(d) inputting the second EEG data into a second machine learning model to determine a second biometric template related to neural activity, the second machine learning model trained using a second training data set of additional EEG data from the data collection participants performing the calibration task;
repeatedly while the user is wearing the headset:
(e) receiving a third EEG data measured from the sensors of the headset;
(f) inputting the third EEG data into the first machine learning model to determine a third biometric template related to the neural activity;
(g) comparing the first and third biometric templates to determine the user's identity;
(h) when the comparing (g) determines the user wearing the headset is not who is logged in, locking the headset;
(i) receiving an input to conduct an activity on the headset requiring heightened authentication; and
(i) in response to a requirement for an additional authentication factor to verify the user's identity, comparing the second and third biometric templates to authenticate the user's identity.

6. The non-transitory, tangible computer-readable device of claim 5, wherein the first and second machine learning models comprise a deep learning neural network.

7. The non-transitory, tangible computer-readable device of claim 5, wherein the comparing (g) comprises:
determining a distance between the first and third biometric templates; and
authenticating the user based on the distance.

8. The non-transitory, tangible computer-readable device of claim 5, wherein the requirement for the additional authentication factor comprises:
presenting at least a portion of the enrollment stimulus or instruction to challenge the user for further authentication;
when the user is challenged, receiving a fourth EEG data collected from the sensors;
inputting the fourth EEG data into the second machine learning model to determine a fourth biometric template related to the neural activity; and
comparing the second and fourth biometric templates to further verify the user's identity.

9. A computer-implemented method for authenticating a user, comprising:
during enrollment:
(a) receiving a first neural data collected from sensors attached to a headset;
(b) inputting the first neural data into a first machine learning model to determine a first biometric template related to neural activity, the first machine learning model trained using a first training data set of additional neural data from data collection participants to maximize distinctiveness;
(c) when an enrollment stimulus or instruction is presented to the user to engage in a calibration task, receiving a second neural data collected from the sensors;
(d) inputting the second neural data into a second machine learning model to determine a second biometric template related to neural activity, the second machine learning model trained using a second training data set of additional neural data from the data collection participants performing the calibration task;

repeatedly while the user is wearing the headset:
(e) receiving a third neural data measured from the sensors;
(f) inputting the EEG third neural data into the first machine learning model to determine a third biometric template related to the neural activity;
(g) comparing the first and third biometric templates to determine the user's identity;
(h) when the comparing (g) determines the user wearing the headset is not who is logged in, locking the headset;
(i) receiving an input to conduct an activity on the headset requiring heightened authentication; and
(i) in response to a requirement for an additional authentication factor to verify the user's identity, comparing the second and third biometric templates to authenticate the user's identity.

\* \* \* \* \*

UNITED STATES PATENT AND TRADEMARK OFFICE
CERTIFICATE OF CORRECTION

PATENT NO. : 12,386,938 B2  
APPLICATION NO. : 19/003945  
DATED : August 12, 2025  
INVENTOR(S) : Littwin et al.

Page 1 of 1

It is certified that error appears in the above-identified patent and that said Letters Patent is hereby corrected as shown below:

In the Claims

In Column 23, Claim 5, Line 62, delete "into at least one" and insert -- into --, therefor.

In Column 23, Claim 5, Line 64, delete "first at least one" and insert -- first --, therefor.

In Column 24, Claim 5, Line 24, delete "(i)" and insert -- (j) --, therefor,

In Column 25, Claim 9, Line 6, delete "EEG third" and insert -- third --, therefor.

In Column 25, Claim 9, Line 15, delete "(i)" and insert -- (j) --, therefor.

Signed and Sealed this  
Twenty-eighth Day of October, 2025

John A. Squires  
*Director of the United States Patent and Trademark Office*